United States Patent [19]
Kishore et al.

[11] Patent Number: 4,971,908
[45] Date of Patent: Nov. 20, 1990

[54] GLYPHOSATE-TOLERANT 5-ENOLPYRUVYL-3-PHOSPHOSHIKIMATE SYNTHASE

[75] Inventors: Ganesh M. Kishore, Chesterfield; Dilip M. Shah, Creve Coeur, both of Mo.

[73] Assignee: Monsanto Company, St. Louis, Mo.

[21] Appl. No.: 179,245

[22] Filed: Apr. 22, 1988

Related U.S. Application Data

[63] Continuation-in-part of Ser. No. 54,337, May 26, 1987, abandoned.

[51] Int. Cl.$^5$ .................. C12N 15/00; C12N 9/10; C07H 21/04
[52] U.S. Cl. ..................... 435/172.1; 435/172.3; 435/193; 536/27; 935/14
[58] Field of Search ............... 435/172.3, 193; 935/14, 935/67, 64

[56] References Cited

U.S. PATENT DOCUMENTS 4,769,061 9/1988 Comai ........................ 71/86

Primary Examiner—Robin Teskin
Assistant Examiner—S. L. Nolan
Attorney, Agent, or Firm—Dennis R. Hoerner, Jr.; Howard C. Stanley; Thomas P. McBride

[57] ABSTRACT

Glyphosate-tolerant 5-enolpyruvyl-3-phosphosikimate (EPSP) synthases, DNA encoding glyhphosate-tolerant EPSP synthases, plant genes encoding the glyphosate-tolerant enzymes, plant transformation vectors containing the genes, transformed plant cells and differentiated transformed plants containing the plant genes are disclosed. The glyphosate-tolerant EPSP synthases are prepared by substituting an alanine residue for a glycine residue in a conserved sequence found between positions 80 and 120 in the mature wild-type EPSP synthase.

15 Claims, 14 Drawing Sheets

```
ATGGAATCCCTGACGTTACAACCCATCGCTCGTGTCGATGGCACTATT
 M  E  S  L  T  L  Q  P  I  A  R  V  D  G  T  I

AATCTGCCCGGTTCCAAGACCGTTTCTAACCGCGCTTTATTGCTGGCG
 N  L  P  G  S  K  T  V  S  N  R  A  L  L  A

GCATTAGCACACGGCAAAACAGTATTAACCAATCTGCTGGATAGCGAT
 A  L  A  H  G  K  T  V  L  T  N  L  L  D  S  D

GACGTGCGCCATATGCTGAATGCATTAACAGGGTTAGGGGTAAGCTAT
 D  V  R  H  M  L  N  A  L  T  G  L  G  V  S  Y

ACGCTTTCAGCCGATCGTACGCGTTGCGAAATTATCGGTAACGGCGGT
 T  L  S  A  D  R  T  R  C  E  I  I  G  N  G  G

CCATTACACGCAGAAGGTGCCCTGGAGTTGTTCCTCGGTAACGCCG (G>C) A
 P  L  H  A  E  G  A  L  E  L  F  L  G  N  A   G¹>A²

ACGGCAATGCGTCCGCTGGCGGCAGCTCTTTGTCTGGGTAGCAATGAT
 T  A  M  R  P  L  A  A  A  L  C  L  G  S  N  D

ATTGTGCTGACCGGTGAGCCGCGTATGAAAGAACGCCCGATTGGTCAT
 I  V  L  T  G  E  P  R  M  K  E  R  P  I  G  H

CTGGTGGATGCTCTGCGCCTGGGCGGGGCGAAGATCACTTACCTGGAA
 L  V  D  A  L  R  L  G  G  A  K  I  T  Y  L  E

CAAGAAAATTATCCGCCGTTGCGTTTACAGGGCGGCTTTACCGGCGGC
 Q  E  N  Y  P  P  L  R  L  Q  G  G  F  T  G  G

AACGTTGACGTTGATGGCTCCGTTTCCAGCCAATTCCTCACCGCACTG
 N  V  D  V  D  G  S  V  S  S  Q  F  L  T  A  L

TTAATGACTGCGCCTCTTGCGCCGGAAGATACGGTGATTCGTATTAAA
 L  M  T  A  P  L  A  P  E  D  T  V  I  R  I  K

GGCGATCTGGTTTCTAAACCTTATATCGACATCACACTCAATCTGATG
 G  D  L  V  S  K  P  Y  I  D  I  T  L  N  L  M

AAGACGTTTGGTGTTGAAATTGAAAATCAGCACTATCAACAATTTGTC
 K  T  F  G  V  E  I  E  N  Q  H  Y  Q  Q  F  V

GTAAAAGGCGGGCAGTCTTATCAGTCTCCGGGTACTTATTTGGTCGAA
 V  K  G  G  Q  S  Y  Q  S  P  G  T  Y  L  V  E

GGCGATGCATCTTCGGCTTCTTACTTTCTGGCAGCAGCAGCAATCAAA
 G  D  A  S  S  A  S  Y  F  L  A  A  A  A  I  K

GGCGGCACTGTAAAAGTGACCGGTATTGGACGTAACAGTATGCAGGGT
 G  G  T  V  K  V  T  G  I  G  R  N  S  M  Q  G

GATATTCGCTTTGCTGATGTGCTGGAAAAAATGGGCGCGACCATTTGC
 D  I  R  F  A  D  V  L  E  K  M  G  A  T  I  C

TGGGGCGATGATTATATTTCCTGCACGCGTGGTGAACTGAACGCTATT
 W  G  D  D  Y  I  S  C  T  R  G  E  L  N  A  I
```

FIGURE 1a

```
GATATGGATATGAACCATATTCCTGATGCGGCGATGACCATTGCCACG
D   M   D   M   N   H   I   P   D   A   A   M   T   I   A   T

GCGGCGTTATTTGCAAAAGGCACCACCAGGCTGCGCAATATCTATAAC
A   A   L   F   A   K   G   T   T   R   L   R   N   I   Y   N

TGGCGTGTTAAAGAGACCGATCGCCTGTTTGCGATGGCAACAGAACTG
W   R   V   K   L   T   D   R   L   F   A   M   A   T   L   L

CGTAAAGTCGGCGCGGAAGTGGAAGAGGGGCACGATTACATTCGTATC
R   K   V   G   A   E   V   E   E   G   H   D   Y   I   R   I

ACTCCTCCGGAAAAACTGAACTTTGCCGAGATCGCGACATACAATGAT
T   P   P   E   K   L   N   F   A   E   I   A   T   Y   N   D

CACCGGATGGCGATGTGTTTCTCGCTGGTGGCGTTGTCAGATACACCA
H   R   M   A   M   C   F   S   L   V   A   L   S   D   T   P

GTGACGATTCTTGATCCCAAATGCACGGCCAAAACATTTCCGGATTAT
V   T   I   L   D   P   K   C   T   A   K   T   F   P   D   Y

TTCGAGCAGCTGGCGCGGATTAGCCAGGCAGCC
F   E   Q   L   A   R   I   S   Q   A   A
```

1. *E. coli* 11303 wild type
2. *E. coli* 11303 SM-1 mutant

FIGURE 1b

```
                   1                                                      50
         Yeast   ...TLVYPFK DIPADQQKVV IPPGSKSISN RALILAALGE GQCKIKNLLH
    Aspergillus  .PS..IEVHP GVAHSSNVIC APPGSKSISN RALVLAALGS GTCRIKNLLH
        Petunia  KPS...EIVL QPIKEISGTV KLPGSKSLSN RILLLAALSE GTTVVDNLLS
         Tomato  KPH...EIVL XPIKDISGTV KLPGSKSLSN RILLLAALSE GRTVVDNLLS
    Arabidopsis  KAS...EIVL QPIREISGLI KLPGSKSLSN RILLLAALSE GTTVVDNLLN
    Glycine max  KPSTSPEIVL EPIKDFSGTI TLPGSKSLSN RILLLAALSE GTTVVDNLLY
          Maize  ..AGAEEIVL QPIKEISGTV KLPGSKSLSN RILLLAALSE GTTVVDNLLN
         E.coli  MES....LTL QPIARVDGTI NLPGSKTVSN RALLLAALAH GKTVLTNLLD
     Salmonella  MES....LTL QPIARVDGAI NLPGSKSVSN RALLLAALAC GKTALTNLLD
      Consensus  ---------- ---------- --PGSK--SN R-L-LAAL-- G-----NLL- 51                                                    100
         Yeast   SDDTKHMLTA VHEL....KG ATISWEDNGE TVVVEGHGGS TLSACADPLY
    Aspergillus  SDDTEVMLNA LERLG....A ATFSWEEEGE VLVVNGKGG. NLQASSSPLY
        Petunia  SDDIHYMLGA LKTLGLHVEE DSANQRAVVE GCGGLFPVG. KESKEEIQLF
         Tomato  SDDIHYMLGA LKTLGLHVED DNENQRAIVE GCGGQFPVG. KKSEEEIQLF
    Arabidopsis  SDDINYMLDA LKRLGLNVET DSENNRAVVE GCGGIFP.AS IDSKSDIELY
    Glycine max  SEDIHYMLGA LRTLGLRVED DKTTKQAIVE GCGGLFP.TS KESKDEINLF
          Maize  SEDVHYMLGA LRTLGLSVEA DKAAKRAVVV GCGGKFPV.. EDAKEEVQLF
         E.coli  SDDVRHMLNA LTALGVSYTL SADRTRCEII GNGG.....P LHAEGALELF
     Salmonella  SDDVRHMLNA LSALGINYTL SADRTRCDIT GNGG.....A LRAPGALELF
      Consensus  SDD---ML-A ---L------ ---------- ---------- --------L-

101                                                   150
         Yeast   LGNAGTASRF LTSLAALVNS TSSQKYIVLT GNARMQQRPI APLVDSLRAN
    Aspergillus  LGNAGTASRF LTTVATLANS .STVDSSVLT GNNRMKQRPI GDLVDALTAN
        Petunia  LGNAGTAMRP LTAAVTVAGG ...NSRYVLD GVPRMRERPI SDLVDGLKQL
         Tomato  LGNAGTAMRP LTAAVTVAGG ...HSRYVLD GVPRMRERPI GDLVDGLKQL
    Arabidopsis  LGNAGTAMRP LTAAVTAAGG ...NARYVLD GVPRMRERPI GDLVVGLKQL
    Glycine max  LGNAGTAMRP LTAAVVAAGG ...NASYVLD GVPRMRERPI GDLVAGLKQL
          Maize  LGNAGTAMRP LTAAVTAAGG ...NATYVLD GVPRMRERPI GDLVVGLKQL
         E.coli  LGNAGTAMRP LAAA..CLG S...N.DIVLT GEPRMKERPI GHLVDALRLG
     Salmonella  LGNAGTAMRP LAA....ALC LGQN.EIVLT GEPAMLERPI GHLVDSLRQG
      Consensus  LGNAGTA-R- L--------- -------VL- G---M--RPI --LV--L---

151                                                   200
         Yeast   GTKIEYLNNE GSLPIKVYTD SVFKGGRIEL AATVSSQYVS SILMCAPYAE
    Aspergillus  VLPLNTSKGR ASLPLKIAAS GGFAGGNINL AAKVSSQRVS SLLMCAPYAK
        Petunia  GAEVDCFLGT KCPPVRIVSK GGLPGGKVKL SGSISSQYLT ALLMAAPLA.
         Tomato  GAEVDCSLGT NCPPVRIVSK GGLPGGKVKL SGSISSQYLT ALLMAAPLA.
    Arabidopsis  GADVECTLGT NCPPVRVNAN GGLPGGKVKL SGSVSSQYLT ALLMSAPLA.
    Glycine max  GADVDCFLGT NCPPVRVNGK GGLPGGKVKL SGSVSSQYLT ALLMAAPLA.
          Maize  GADVDCFLGT DCPPVRVNGI GGLPGGKVKL SGSISSQYLS ALLMAAPLA.
         E.coli  GAKITYLEQE NYPPLR..LQ GGFTGGNVDV DGSVSSQFLT ALLMTAPLAP
     Salmonella  GANIDYLEQE NYPPLR..LR GGFTGGDIEV DGSVSSQFLT ALLMTAPIA.
      Consensus  ---------- ---P------ ----GG---- ----SSQ--- --LM-AP-A-

201                                                   250
         Yeast   EPVTLALVGG KPISKLYVDM TIKMMEKFGI NVETSTTEPY TYYIPKGHYI
    Aspergillus  EPVTLRVLGG KPISQPYIDM TTAMMRSFGI DVQKSTTEEH TYHIPQGRYV
        Petunia  LGDVEIEIID KLISVPYVEM TLKLMERFGI SVEHSSSWDR FFVRGGQKYK
         Tomato  LGDVEIEIID KLISVPYVEM TLKLMERFGV FVEHSSGWDR FLVKGGQKYK
    Arabidopsis  LGDVEIEIVD KLISVPYVEM TLKLMERFGV SVEHSDSWDR FFVKGGQKYK
    Glycine max  LGDVEIEIVD KLISVPYVEM TLKLMERFGV SVEHSGNWDR FLVHGGQKYK
          Maize  LGDVEIEIID KLISIPYVEM TLRLMERFGV KAEHSDSWDR FYIKGGQKYK
         E.coli  E.DTVIRIKG DLVSKPYIDI TLNLMKTFGV EIE.NQHYQQ FVVKGGQSYQ
     Salmonella  PKDTIIRVKG ELVSKPYIDI TLNLMKTFG. VEIANHHYQQ FVVKGGQQYH
      Consensus  ---------- ---S--Y--- T---M--FG- ---------- -------Y-
```

FIGURE 2(a)

```
                251                                                              300
     Yeast      NPSEYVIESD ASSATYPLAF AMMTGTTVTV PNIGFESLQG DARFARDVLK
Aspergillus     NPAEYVIESD ASCATYPLAV AAVTGTTCTV PNIGSASLQG DARFAVEVLR
    Petunia    SPGKAFVEGD ASSASYFLAG AAVTGGTITV EGCGTNSLQG DVKFA.EVLE
     Tomato    SPGKAFVEGD ASSASYFLAG AAVTGGTVTV EGCGTSSLQG DVKFA.EVLE
Arabidopsis     SPGNAYVEGD ASSACYFLAG AAITGETVTV EGCGTTSLQG DVKFA.EVLE
   Brassica    SPGNAFVEGD ASSASYLLAG AAITGGTITV NGCGTSSLQG DVKFA.EVLE
      Maize    SPKNAYVEGD ASSATYFLAG AAITGGTVTV EGCGTTSLQG DVKFA.EVLE
     E.coli    SPGTYLVEGD ASSASYFLAA AAIKGGTVKV TGIGRNSMQG DIRFA.DVLE
  Salmonella   SPGRYLVEGD ASSASYFLAA GAIKGGTVKV TGIGRKSMQG DIRFA.DVLE
  Consensus    -P-----E-D AS-A-Y-LA- -A--G-T--V ---G--S-QG D--FA--VL- 301                                                              350
     Yeast      PMGCKITQTA TSTTVSGPPV GTLKPLKHVD MEPMTDAFLT ACVVAAISHD
Aspergillus     PMGCTVEQTE TSTTVTGPSD GIL.RATSKR GYGTNDRCVP RCFRTGSHRP
    Petunia    KMGAEVTWTE NSVTVKGPPR SSSGR.KHLR AIDVNMNKMP DVAMTLAVVA
     Tomato    KMGAEVTWTE NSVTVKGPPR NSSG.MKHLR AIDVNMNKMP DVAMTLAVVA
Arabidopsis     KMGCKVSWTE NSVTVTGPPR DAFG.MRHLR AIDVNMNKMP DVAMTLAVVA
   Brassica    KMGAKVTWSE NSVTVSGPPR DFSGR.KVLR GIDVNMNKMP DVAMTLAVVA
      Maize    MMGAKVTWTE TSVTVTGPPR SHFGR.KHLK AIDVNMNKMP DVAMTLAVVA
     E.coli    KMGATICW.. ......GDDY ISCTR.GELN AIDMDMNHIP DAAMTIATAA
  Salmonella   LMGATITW.. ......GDDF IACTR.GELH AIDMDMNHIP DAAMTLATTA
  Consensus    -MG------- ------G--- ---------- ---------- ----------

351                                                              400
     Yeast      SDPNSANTTT IEGIANQRVK ECNRILAMAT ELAKFGVKTT ELPDGIQVHG
Aspergillus     MEKSQTTPPV SSGIANQRVK ECNRIKAMKD ELAKFGVICR EHDDG.....
    Petunia    LYADGPT..A IRDVASWRVK ETERMIAICT ELRKLGATVE EGPD......
     Tomato    LFADGPT..T IRDVASWRVK ETERMIAICT ELRKLGATVV EGSD......
Arabidopsis     LFADGPT..T IRDVASWRVK ETERMIAICT ELRKLGATVE EGSD......
   Brassica    LFANGPT..A IRDVASWRVK ETERMIAICT ELRKLGATVE EGPD......
      Maize    LFADGPT..A IRDVASWRVK ETERMVAIRT ELTKLGASVE EGPD......
     E.coli    LFAKGTT..R LRNIYNWRVK ETDRLFAMAT ELRKVGAEVE EGHD......
  Salmonella   LFAKGTT..T LRNIYNWRVK ETDRLFAMAT ELRKVGAEVE EGHD......
  Consensus    ---------- -------RVK E--R--A--- EL-K-G---- E--D------

401                                                              450
     Yeast      LNSIKDLKVP SDSSGPVGVC TYDDHRVAMS FSLLAGMVNS QNERDEVANP
Aspergillus     .LEIDGIDRS NLRQPVGGVP CYDDHRVAFS FSVL...... ...SLVTPQP
    Petunia    YCIITPPEKL N....VTDID TYDDHRMAMA FS........ ..LAACADVP
     Tomato    YCIITPPEKL N....VTEID TYDDHRMAMA FS........ ..LAACADVP
Arabidopsis     YCVITPPKK. ...VKTAEID TYDDHRMAMA FS........ ..LAACADVP
   Brassica    YCVITPPEKL N....VTAID TYDDHRMAMA FS........ ..LAACGDVP
      Maize    YCIITPPEKL N....VTAID TYDDHRMAMA FS........ ..LAACAEVP
     E.coli    YIRITPPEKL N....FAEIA TYNDHRMAMC FS........ ..LVALSDTP
  Salmonella   YIRITPPAKL ....QHADIG TYNDHRMAMC FS........ ..LVALSDTP
  Consensus    ---I------ --------I- -Y-DHR-A-- FS-------- ---------P 451           478
     Yeast      VRILERHCTG KTWPGWWDVL HSELGA..
Aspergillus     TLILEKECVG KTWPGWWDTL RQLFKV..
    Petunia    VTINDPGCTR KTFPNYFDVL QQYSKI*.
     Tomato    VTIKNPGCTR KTFPDYFEVL QKYSKH*.
Arabidopsis     ITINDSGCTR KTFPDYFQVL ERITKH..
   Brassica    VTIKDP.CTR KTFPDYFEVL ERLTKH*.
      Maize    VTIRDPGCTR KTFPDYFDVL STFVKN*.
     E.coli    VTILDPKCTA KTFPDYFEQL ARISQAA*
  Salmonella   VTILDPKCTA KTFPDYFEQL ARMSTPA.
  Consensus    --I-----C-- KT-P--F--L --------
```

FIGURE 2(b)

CaMV 35S PROMOTER

```
        Filled EcoRI                                            60
1       |         .          .          .          .          .
GAATTAATTCCCGATCCTATCTGTCACTTCATCAAAAGGACAGTAGAAAAGGAAGGTGGC 120
        .          .          .          .          .          .
ACTACAAATGCCATCATTGCGATAAAGGAAAGGCTATCGTTCAAGATGCCTCTGCCGACA 180
        .          .          .          .          .          .
GTGGTCCCAAAGATGGACCCCCACCCACGAGGAGCATCGTGGAAAAAGAAGACGTTCCAA 240
        .          .          .          .          .          .
CCACGTCTTCAAAGCAAGTGGATTGATGTGATATCTCCACTGACGTAAGGGATGACGCAC TATA
                                   |                          300
        .          .          .   |      .          .          .
AATCCCACTATCCTTCGCAAGACCCTTCCTCTATATAAGGAAGTTCATTTCATTTGGAGA 5' mRNA
    |                               332
    |          .          .
GGACACGCTGAAATCACCAGTCTCTCTCTACA
```

SYNTHETIC MULTI-LINKER

```
    BglII  ClaI SmaI KpnI SalI EcoRI
     |      |    |    |    |    |
    AGATCTATCGATTCCCGGGTACCTCGAGAATTCCC
```

NOS 3'

```
      368          .          .          .          .        420
                 GATCGTTCAAACATTTGGCAATAAAGTTTCTTAAGATTGAATCCTGTTGCCGG

.          .          .          .          .        480
TCTTGCGATGATTATCATATAATTTCTGTTGAATTACGTTAAGCATGTAATAATTAACAT

3' End mRNA
                                           |  |   ||||||       540
        .          .          .          .  |  |   ||||||      .
GTAATGCATGACGTTATTTATGAGATGGGTTTTTATGATTAGAGTCCCGCAATTATACAT

600
        .          .          .          .          .          .
TTAATACGCGATAGAAAACAAAATATAGCGCGCAAACTAGGATAAATTATCGCGCGCGGT

HindIII
                                                   641| 648
        .          .          .
TCATCTATGTTACTAGATCggggatccgtcgacctgcagccaagctt
```

FIGURE 4

GLYPHOSATE-TOLERANT 5-ENOLPYRUVYL-3-PHOSPHOSHIKIMATE SYNTHASE

This application is a continuation-in-part of co-pending application Ser. No. 054,337, filed May 26, 1987, now abandoned.

BACKGROUND OF THE INVENTION

Recent advances in genetic engineering have provided the requisite tools to transform plants to contain foreign genes. It is now possible to produce plants which have unique characteristics of agronomic importance. Certainly, one such advantageous trait is herbicide tolerance. Herbicide-tolerant plants could reduce the need for tillage to control weeds thereby effectively reducing costs to the farmer.

One herbicide which is the subject of much investigation in this regard is N-phosphonomethylglycine.

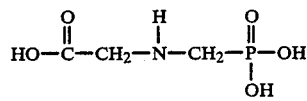

This herbicide is a non-selective, broad spectrum, post-emergence herbicide which is registered for use in more than fifty crops. This molecule is an acid, which dissociates in aqueous solution to form phytotoxic anions. Several anionic forms are known. As used herein, the name "glyphosate" refers to the acid and its anions.

Glyphosate inhibits the shikimic acid pathway which provides a precursor for the synthesis of aromatic amino acids. Specifically, glyphosate curbs the conversion of phosphoenolpyruvate and 3-phosphoshikimic acid to 5-enolpyruvyl-3-phosphoshikimic acid by inhibiting the enzyme 5-enolpyruvyl-3phosphoshikimate synthase.

It has been shown that glyphosate tolerant plants can be produced by inserting into the genome of the plant the capacity to produce a higher level of EPSP synthase.

The present invention provides a means of enhancing the effectiveness of glyphosate-tolerant plants by producing mutant EPSP synthase enzymes which exhibit a lower affinity for glyphosate while maintaining catalytic activity.

BRIEF DESCRIPTION OF THE DRAWINGS

FIGS. 1A and 1B show the amino acid sequences for the EPSP synthase enzymes from *E. coli* 11303 and *E. coli* 11303 SM-1.

FIGS. 2A and 2B show the amino acid sequences for EPSP synthase enzymes from various plant, bacteria and fungal species.

FIG. 4 shows the sequence for the CaMV35S promoter, synthetic multi-linker and NOS3' transcription terminator/polyadenylation signal used in the vectors described herein.

STATEMENT OF THE INVENTION

Figure 3:
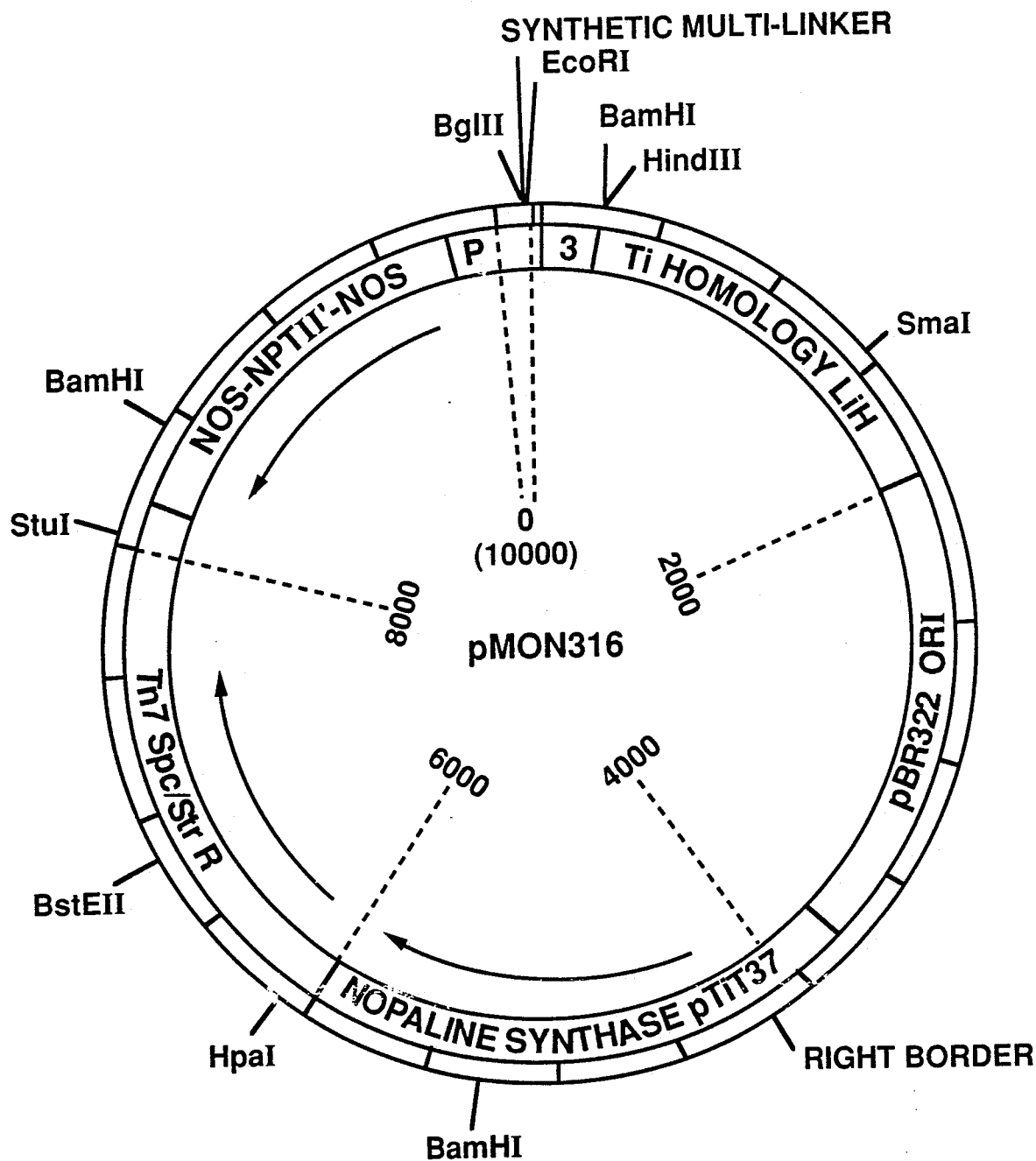
FIG. 3 shows a plasmid map for co-integrating plant transformation vector pMON316.

The present invention provides novel EPSP synthase enzymes which exhibit increased tolerance to glyphosate herbicide. The subject enzymes of this invention have an alanine for glycine substitution as described hereinafter.

The present invention was enabled in part by the discovery of an *E. coli* bacteria carrying an altered EPSP synthase gene. This organism was obtained in the following manner.

Cells of *E. coli* ATCC 11303 were transferred to medium A and incubated at 37° C.

| MEDIUM A | |
|---|---|
| 10X MOPS[1] medium | 50 ml |
| 50% glucose solution (50 g/100 ml) | 2 ml |
| 100 mM aminomethyl phosphonate (sodium salt) | 10 ml |
| Thiamine (5 mg/ml) pH 7.4 | 1 ml |
| 100 mM glyphosate (sodium salt) | 10 ml |
| Deionized water to | 500 ml |
| 10X MOPS medium: | |
| Per 500 ml | |
| 1 M MOPS (209.3 g/l, pH 7.4) | 200 ml |
| 1 M Tricine (89.6 g/l, pH 7.4) | 20 ml |
| 0.01 M FeSO$_4$.7H$_2$O (278.01 mg/100 ml) | 5 ml |
| 1.9 M NH$_4$Cl (50.18 g/500 ml) | 25 ml |
| 0.276 M K$_2$SO$_4$ (4.81 g/100 ml) | 5 ml |
| 0.5 mM CaCl$_2$.2H$_2$O (7.35 mg/100 ml) | 5 ml |
| 0.528 M MgCl$_2$ (10.73 g/100 ml) | 5 ml |
| 5 M NaCl (292.2 g/l) | 50 ml |
| 0.5% L-Methionine (500 mg/100 ml) | 5 ml |
| micronutrients* | |
| *micronutrients in 25 ml H$_2$O | |
| ZnSO$_4$ (2.88 mg/ml) | 25 μl |
| MnCl$_2$ (1.58 mg/ml) | 250 μl |
| CuSO$_4$ (1.6 mg/ml) | 25 μl |
| CoCl$_2$ (7.14 mg/ml) | 25 μl |
| H$_3$BO$_3$ (2.47 mg/ml) | 250 μl |
| NH$_4$Mo$_7$O$_{24}$ (3.71 mg/ml) | 25 μl |

[1]MOPS - 3-N-morpholino-propane-sulfonic acid

After a week, a culture was obtained which could grow rapidly in the presence of high concentrations of glyphosate in the growth medium (10 mM or higher). Analysis of the EPSP synthase activity in the extracts of this culture and comparison of its glyphosate sensitivity with that of wild-type *E. coli* ATCC 11303 revealed that the mutant organism had an altered EPSP synthase. The glyphosate sensitivity of EPSP synthase of mutant cells was significantly different from that of wild-type cells. This mutant bacterium was designated *E. coli* 11303 SM-1. The AroA gene encoding EPSP synthase from this mutant bacterium was isolated as follows.

The DNA from this bacterium was isolated by the method of Marmur (1961). Southern hybridization using *E. coli* K-12 aroA gene (Rogers et al., 1983) as the probe established that the aroA gene in the mutant bacterium was on a 3.5 Kb BglII-HindIII fragment. This fragment was cloned into the vector pKC7 (Rao, R. N. & Rogers, 1979) and the resulting plasmid was used for transformation of *E. coli*. Transformed colonies were screened for their ability to grow in the presence of glyphosate (Medium A) and were shown to contain the 3.5 Kb BglII-HindIII insert by hybridization with the *E. coli* K-12 aroA gene. This clone was designated pMON9538.

The nucleotide sequence for the mutant *E. coli* EPSP synthase aroA gene was determined by the method of Sanger (1977) and the corresponding amino acid sequence for the encoded EPSP synthase deduced therefrom.

All peptide structure represented in the present specification and claims are shown in conventional format wherein the amino group at the N-terminus appears to the left and the carboxyl group at the C-terminus at the right. Likewise, amino acid nomenclature for the naturally occurring amino acids found in protein is as follows: alanine (ala;A), asparagine (Asn;N), aspartic acid (Asp;D), arginine (Arg;R), cysteine (Cys;C), glutamic acid (Glu;E), glutamine (Gln;Q), glycine (Gly;G), histidine (His;H), isoleucine (Ile;I), leucine (Leu;L), lysine (lys;K), methionine (Met;M), phenylalanine (Phe;F), proline (Pro;P), serine (Ser;S), threonine (Thr;T), tryptophan (Trp;W), tyrosine (Tyr;Y) and valine (Val;V).

Amino acid and nucleotide sequences for the above-described mutant and the wild-type EPSP synthase enzymes of *E. coli* are shown in FIG. 1. The mutant *E. coli* EPSP synthase sequence has an alanine for glycine substitution at position 96.

FIG. 2 shows the amino acid sequence for EPSP synthase from various plant, bacteria and fungal species. Inspection of the sequences and alignment to maximize the similarity of sequence reveals a region of highly conserved amino acid residues (indicated by the box) in the region of the *E. coli* EPSP synthase mutant where the alanine for glycine substitution occurred. Indeed, all EPSP synthase enzymes reported in the literature and in the present specification reveal a glycine at this position in this highly conserved region.

Specifically, the glycine residue which is substituted with the alanine residue in the preparation of the glyphosate-tolerant EPSP synthases of the present invention occurs at position 97 in the EPSP synthase of *Aspergillus nidulans* (Charles et al., 1986); position 101 in the EPSP synthase of petunia; position 101 in the EPSP synthase of tomato; position 101 in the EPSP synthase of *Arabidopsis thaliana*; position 104 in the EPSP synthase of Glycine max; position 96 in the EPSP synthase of *E. coli* K-12 (Duncan et al., 1984) and position 96 in the EPSP synthase of *Salmonella typhimurium* (Stalker et al., 1985).

Figure 11:
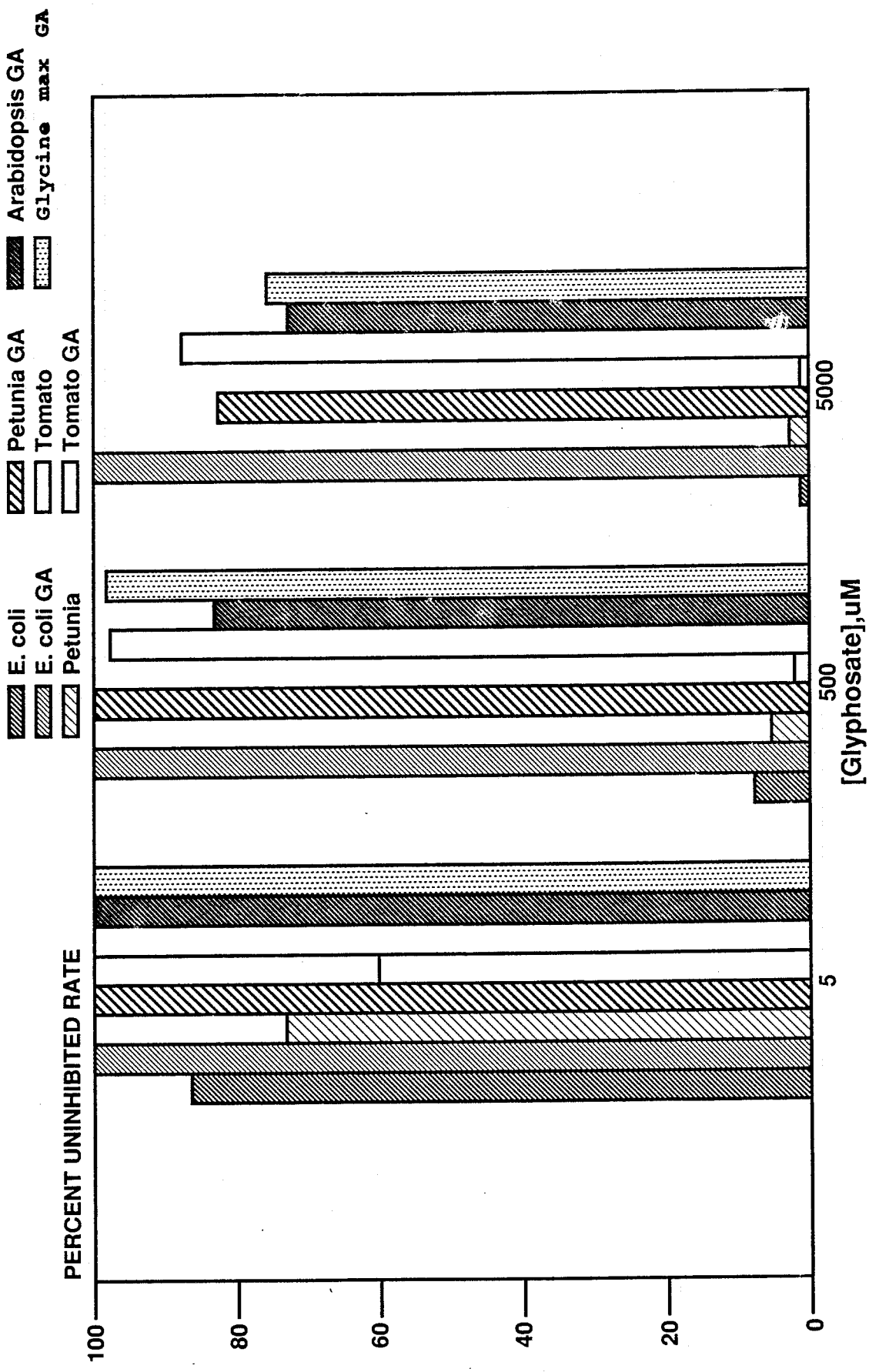
FIG. 11 shows representative inhibition data for glyphosate-tolerant EPSP synthase versus wild-type EPSP synthases.

It has been found that the alanine for glycine substitution can be introduced into this highly conserved region of other wild-type EPSP synthase enzymes to yield glyphosate-tolerant EPSP synthase enzymes. FIG. 11 shows representative inhibition data for glyphosate-tolerant EPSP synthases of the present invention versus wild-type EPSP synthases.

Hence, in one aspect the present invention provides glyphosate-tolerant EPSP synthase enzymes and a method for producing such enzymes which comprises substituting an alanine residue for the second glycine residue in the highly conserved region having the sequence:

-L-G-N-A-G-T-A- located between positions 80 and 120 in the mature wild-type EPSP synthase amino acid sequence. In most cases the above sequence will be located between positions 90 and 110 in the mature EPSP synthase.

In one embodiment, glyphosate-tolerant EPSP synthase coding sequences are useful in further enhancing the efficacy of glyphosate-tolerant transgenic plants. Methods for transforming plants to exhibit glyphosate tolerance are disclosed in European Patent Office Publication No. 0218571 and commonly assigned U.S. patent application entitled "Glyphosate-Resistant Plants," Ser. No. 879,814 filed July 7, 1986, now allowed, not as yet patented the disclosures of which are specifically incorporated herein by reference. The present invention can be utilized in this fashion by isolating the plant or other EPSP synthase coding sequences and introducing the necessary change in the DNA sequence coding for EPSP synthase to result in the aforementioned alanine for glycine substitution in the translated EPSP synthase enzyme.

In another aspect, the present invention provides a transformed plant cell and plant regenerated therefrom which contain a plant gene encoding a glyphosate-tolerant EPSP synthase enzyme having the sequence:

-L-G-N-A-A-T-A- located between positions 80 and 120 in the mature EPSP synthase amino acid sequence. In most cases the above sequence will be located between positions 90 and 110 in the mature EPSP synthase. The gene further comprises a DNA sequence encoding a chloroplast transit peptide attached to the N-terminus of the mature EPSP synthase coding sequence, said transit peptide adapted to facilitate the import of the EPSP synthase enzyme into the chloroplast of a plant cell.

Therefore, in yet another aspect the present invention also provides a plant transformation or expression vector comprising a plant gene which encodes a glyphosate-tolerant EPSP synthase enzyme having the sequence:

-L-G-N-A-A-T-A- located between positions 80 and 120 in the mature EPSP synthase amino acid sequence.

According to still another aspect of the present invention, a process is provided that entails cultivating such a plant and, in addition, propagating such plant using propagules such as explants, cuttings and seeds or crossing the plant with another to produce progeny that also display resistance to glyphosate herbicide.

The EPSP synthase sequences shown in FIG. 2 represent a broad evolutionary range of source materials for EPSP synthases. These data demonstrate that EPSP synthase polypeptides from bacterial, fungal and plant material contain the aforementioned conserved region (-L-G-N-A-G-T-A-). However, those skilled in the art will recognize that a particular EPSP synthase may be produced by and isolated from another source material which may not have the exact sequence of the conserved region. Indeed, it has been found that an alanine may be inserted for the first glycine of the conserved region of petunia EPSP synthase with no attendant changes in glyphosate sensitivity.

Hence, for purposes of the present invention glyphosate-tolerant EPSP synthase polypeptides produced by substituting an alanine for the second glycine in a sequence homologous to the sequence (-L-G-N-A-G-T-A-) located between positions 80 and 120 is considered an equivalent of the present discovery and therefore within the scope of the invention.

The glyphosate-tolerant EPSP synthase plant gene encodes a polypeptide which contains a chloroplast transit peptide (CTP), which enables the EPSP synthase polypeptide (or an active portion thereof) to be transported into a chloroplast inside the plant cell. The EPSP synthase gene is transcribed into mRNA in the nucleus and the mRNA is translated into a precursor polypeptide (CTP/mature EPSP synthase) in the cytoplasm. The precursor polypeptide (or a portion thereof) is transported into the chloroplast.

Suitable CTP's for use in the present invention may be obtained from various sources. Most preferably, the CTP is obtained from the endogenous EPSP synthase gene of the subject plant to be transformed. Alternately, one may also use a CTP from an EPSP synthase gene of another plant. Although there is little homology between the CTP sequences of the EPSP synthase gene and the ssRUBISCO gene (see e.g., Broglie, 1983), one may find that non-homologous CTPs may function in particular embodiments. Suitable CTP sequences for use in the present invention can be easily determined by assaying the chloroplast uptake of an EPSP synthase polypeptide comprising the CTP of interest as described in Example 18 hereinafter.

Suitable plants for the practice of the present invention include, but are not limited to, soybean, cotton, alfalfa, oil seed rape, flax, tomato, sugar beet, sunflower, potato, tobacco, maize, wheat, rice and lettuce.

Promoters which are known or found to cause transcription of the EPSP synthase gene in plant cells can be used in the present invention. Such promoters may be obtained from plants or viruses and include, but are not necessarily limited to, the 35S and 19S promoters of cauliflower mosaic virus and promoters isolated from plant genes such as EPSP synthase, ssRUBISCO genes and promoters obtained from T-DNA genes of *Agrobacterium tumefaciens* such as nopaline and mannopine synthases. The particular promoter selected should be capable of causing sufficient expression to result in the production of an effective amount of EPSP synthase polypeptide to render the plant cells and plants regenerated therefrom substantially resistant to glyphosate. Those skilled in the art will recognize that the amount of EPSP synthase polypeptide needed to induce tolerance may vary with the type of plant.

The promoters used in the EPSP synthase gene of this invention may be further modified if desired to alter their expression characteristics. For example, the CaMV35S promoter may be ligated to the portion of the ssRUBISCO gene which represses the expression of ssRUBISCO in the absence of light, to create a promoter which is active in leaves but not in roots. The resulting chimeric promoter may be used as described herein. As used herein, the phrase "CaMV35S" promoter includes variations of CaMV35S promoter, e.g. promoters derived by means of ligation with operator regions, random or controlled mutagenesis, addition or duplication of enhancer sequences, etc.

The mutant EPSP synthase polypeptides of the present invention may be prepared by either polypeptide synthesis or isolation and mutagenesis of a EPSP synthase gene to produce the above described glyphosate-tolerant molecule. Since it is foreseen that the greatest utility of the present invention is in the preparation of glyphosate-tolerant plants, nucleotide sequences (either cDNA or genomic) encoding the glyphosate-tolerant EPSP synthase can be easily prepared in the following manner.

cDNA Coding Sequences

Total RNA is isolated from the source material which includes, but is not necessarily limited to, bacteria, fungi and plant tissue. PolyA-mRNA is selected by oligodT cellulose chromatography. A cDNA library is then prepared using the polyA-mRNA. The cDNA library is then screened using a previously cloned EPSP synthase sequence or a suitable oligonucleotide probe. Suitable oligonucleotide probes include probes based on the conserved region having the amino acid sequence (L-G-N-A-G-T-A) or probes based on the amino acid sequence of other portions of the EPSP synthase molecule. The cDNA fragments selected by hybridization are then sequenced to confirm that the fragment encodes the EPSP synthase and to determine the DNA sequence encoding and adjacent to the conserved amino acid sequence described above.

The EPSP synthase clone is then altered by oligonucleotide mutagenesis to insert the DNA substitution necessary to result in the alanine for glycine substitution in the conserved amino acid sequence (L-G-N-A-G-T-A). The above procedure produces a cDNA sequence which encodes the glyphosate-tolerant EPSP synthase of the present invention based on the wildtype EPSP synthase of the selected source material. This structural coding sequence can be inserted into functional chimeric gene constructs and inserted into suitable plant transformation vectors to be used in preparing transformed plant cells and regenerated plants using the methodology described herein.

Genomic EPSP Synthase Clone

Generally it is preferred that the plant tissue from the plant species to be transformed also serve as the source material for the DNA coding sequence for the glyphosate-tolerant EPSP synthase of the present invention. In this way, one would easily obtain the chloroplast transit peptide coding sequence from the plant species to be transformed. In some cases, it may be beneficial to utilize a genomic clone from the plant species which comprises the introns normally found in the endogenous EPSP synthase gene. The general method described above is also applicable with the exception that the probes are used to screen a genomic DNA library constructed from the selected plant tissue. Detailed examples better elucidating this preparation of cDNA and genomic DNA glyphosate-tolerant EPSP synthase constructs of the present invention are provided below.

PREPARATION OF EPSP SYNTHASE PLANT TRANSFORMATION VECTORS

I. EPSP Synthase of Petunia

A. Creation of MP4-G Cell Line

The starting cell line, designated as the MP4 line, was derived from a Mitchell diploid petunia (see e.g., Ausubel 1980). The MP4 cells were suspended in Murashige and Skoog (MS) culture media, (GIBCO, Grand Island, N.Y.) All transfers involved dispensing 10 ml of suspension cultures into 50 ml of fresh media. Cultivation periods until the next transfer ranged from 10 to 14 days, and were based on visual indications that the culture was approaching saturation.

Approximately 10 ml of saturated suspension culture (containing about $5 \times 10^6$ cells) were transferred into 50 ml of MS media containing 0.5 mM glyphosate. The sodium salt of glyphosate was used throughout the experiments described herein. The large majority of cells were unable to reproduce in the presence of the glyphosate. The cells which survived (estimated to be less than 1% of the starting population) were cultured in 0.5 mM glyphosate and transferred to fresh media containing glyphosate every 10 to 14 days.

After two transfers, the surviving cells were transferred into fresh media containing 1.0 mM glyphosate. After two transfers at 1.0 mM, the surviving cells were transferred sequentially into 2.5 mM glyphosate, 5.0 mM glyphosate, and 10 mM glyphosate.

The MP4-G cells prepared as described-above were substantially shown by a Southern blot assay (Southern, 1975) to have about 15–20 copies of the EPSP synthase gene, due to a genetic process called "gene amplification" (see e.g. Schimke 1982). Although spontaneous mutations might have occurred during the replication of any cell, there is no indication that any mutation or other modification of the EPSP synthase gene occurred during the gene amplification process. The only known difference between the MP4 and the MP4-G cells is that the MP4-G cells contain multiple copies of an EPSP synthase gene and possibly other genes located near it on the chromosomes of the cells.

B. Purification and Sequencing of EPSP Synthase Enzymes

Petunia cells from the MP4-G cell line were harvested by vacuum filtration, frozen under liquid $N_2$, and ground to a powder in a Waring blender. The powder was suspended in 0.2 M Tris-HCl, pH 7.8, containing 1 mM EDTA and 7.5% w/v polyvinyl-polypyrrolidone. The suspension was centrifuged at about $20,000 \times$ gravity for 10 min to remove cell debris. Nucleic acids were precipitated from the supernatant by addition of 0.1 volume of 1.4% protamine sulfate and discarded.

The crude protein suspension was purified by five sequential steps (see Mousdale 1984 and Steinrucken 1985) which involved: (1) ammonium sulfate precipitation; (2) diethylaminoethyl cellulose ion exchange chromatography; (3) hydroxyapatite chromatography; (4) hydrophobic chromatography on a phenylagarose gel; and (5) sizing on a Sephacryl S-200 gel.

The purified EPSP synthase polypeptide was degraded into a series of individual amino acids by Edman degradation by a Model 470A Protein Sequencer (Applied Biosystems Inc., Foster City, CA), using the methods described in Hunkapiller 1983a. Each amino acid derivative was analyzed by reverse phase high performance liquid chromatography, as described by Hunkapiller 1983b, using a cyanopropyl column with over 22,000 theoretical plates (IBM Instruments, Wallingford CT). A partial amino acid sequence for petunia EPSP synthase is shown in Table 1.

TABLE 1

PETUNIA EPSP SYNTHASE SEQUENCES

| | 8 | 9 | 10 | 11 | 12 | 13 |
|---|---|---|---|---|---|---|
| Amino Acid: | Gln | Pro | Ile | Lys | Glu | Ile |
| mRNA strand: | 5'-CAP | CCN | AUU | GAP | CAP | AUU |
| | | | C | | | C |
| | | | A | | | A |
| Complementary DNA strand: | 3'-GTQ | GGN | TAA | TTQ | CTQ | TAA |
| | | | G | | | G |
| | | | U | | | U |
| Synthetic DNA Probes: | | | | | | |
| EPSP1: | 3'-GTQ | GGP | TAP | TTQ | CTQ | TA |
| EPSP2: | 3'-GTQ | GGQ | TAP | TTQ | CTQ | TA |
| EPSP3: | 3'-GTQ | GGN | TAT | TTQ | CTQ | TA |
| Exact mRNA Sequence: | 5'-CAA | CCC | AUU | AAA | GAG | AUU |

C. Synthesis of Probes

Using the genetic code, the amino acid sequence indicated in Table 1 was used to determine the possible DNA codons which are capable of coding for each indicated amino acid. Using this information, three different probe mixtures were created and designated as EPSP-1, EPSP-2, and EPSP-3, as shown in Table 1. In this table, A, T, U, C, and G represent the nucleotide bases: adenine, thymine, uracil, cytosine and guanine. The letters P, Q, and N are variables; N represents any of the bases; P represents purines (A or G); Q represents pyrimidines (U, T, or C).

All oligonucleotides were synthesized by the method of Adams 1983. Whenever an indeterminate nucleotide position (P, Q or N) was reached, a mixture of appropriate nucleotides was added to the reaction mixture. Probes were labeled 20 pmol at a time shortly before use with 100 $\mu$Ci $\gamma$-[$^{32}$P]-ATP (Amersham) and 10 units polynucleotide kinase in 50 mM Tris-HCl, pH 7.5; 10 mM $MgCl_2$, 5 mM DTT, 0.1 mM EDTA, and 0.1 mM spermidine. After incubation for 1 hr. at 37° C., the probes were repurified on either a 20% acrylamide, 8 M urea gel or by passage over a 5 ml column of Sephadex G25 in 0.1 M NaCl, 10 mM Tris-HCl, pH 7.5, 1 mM EDTA.

D. Preparation of mRNA and Preliminary Testing of Probes (a) Poly-A mRNA

Total RNA was isolated from the MP4 (glyphosate sensitive) and MP4-G (glyphosate resistant) cell lines as described by Goldberg 1981. Total RNA was further sedimented through a CsCl cushion as described by Depicker 1982. Poly-A mRNA was selected by oligodT cellulose chromatography. The yield of poly-A RNA was 1.1 micrograms ($\mu$g) per gram of MP4 cells and 2.5 $\mu$g/gm of MP4-G cells.

(b) Gel Processing of RNA

Ten $\mu$g of poly-A RNA from the MP4 or MP4-G cell lines were precipitated with ethanol and resuspended in $1 \times$ MOPS buffer (20 mM MOPS, pH 7.0, 5 mM sodium acetate and 1 mM EDTA, ph 8.0) containing 50% formamide and 2.2 M formaldehyde. RNA was denatured by heating at 65° C. for 10 min. One-fifth volume of a loading buffer containing 50% glycerol, 1 mM EDTA, 0.4% bromophenol blue and 0.4% xylene cyanol was then added. RNA was fractionated on a 1.3% agarose gel containing 1.1 M formaldehyde until bromophenol blue was near the bottom. HaeIII-digested φX174 DNA, labelled with $^{32}P$, was run as a size standard. The DNA markers indicated approximate sizes for the RNA bands.

(c) Transfer of RNA to Nitrocellulose

RNA was transferred to nitrocellulose (#BA85, Schleicher & Schuell, Keene, NH) by blotting the gels overnight using 20X SSC (1X SSC is 0.15 M NaCl, 0.015 M sodium citrate, pH 7.0) as the transfer buffer. After transfer, filters were air-dried and baked in a vacuum oven for 2-3 hrs at 80° C.

(d) Preliminary Hybridization with Radioactive Probes

Filters were prehybridized in 6×SSC, 10×Denhardt's solution (1×Denhardt's solution is 0.02% ficoll, 0.02% polyvinylpyrrolidone, 0.02% bovine serum albumin), 0.5% NP-40, and 200 µg/ml E. coli transfer RNA at 50° C. for 4 hrs. Hybridization was carried out in the fresh solution containing $2 \times 10^6$ cpm/ml of either EPSP-1 or EPSP-2 probe for 48 hrs at 32° C. The EPSP-3 probe was not tested since it contained a codon (ATA) that is rarely found in the petunia genome. Hybridization temperature (32° C.) used in each case was 10° C. below the dissociation temperature (Td) calculated for the oligonucleotide with the lowest GC content in a mixture. The Td of the probe was approximated by the formulate $2° C. \times (A+T) + 4° C. \times (G+C)$.

(e) Filter Washing

The filters were washed twice for 15-20 min at room temperature in 6×SSC and then for 5 min at 37° C. with gentle shaking. Filters were then wrapped in plastic film and autoradiographed for 12-14 hrs at −70° C. with two intensifying screens. The filters were then washed again for 5 min with gentle shaking at a temperature of 42° C. The filters were autoradiographed again for 12-14 hrs. The autoradiographs indicated that the probe EPSP-1 hybridized to an RNA of approximately 1.9 kb in the lane containing the poly-A RNA from the MP4-G cell line. No hybridization to this RNA was detected in the lane containing the poly-A RNA from the MP4 cell line. This result was attributed to overproduction of EPSP synthase mRNA by the MP4-G cell line. The probe EPSP-2, which differs from EPSP-1 by a single nucleotide, showed barely detectable hybridization to the 1.9 kb mRNA of the MP4-G cell line but hybridized strongly to a 1.0 kb mRNA from both cell lines. However, the 1.0 kb DNA was not sufficient to encode a polypeptide of 50,000 daltons, and it is believed that one of the sequences in the EPSP-2 probe hybridized to an entirely different sequence in the library. These results suggested that degenerate probe mixture EPSP-1 contained the correct sequence for EPSP synthase. This mixture was used in all subsequent degenerate probe hybridization experiments.

E. Preparation of λgt 10 cDNA library (a) Materials Used

AMV reverse transcriptase was purchased from Seikagaku America, Inc., St. Petersburg, FL; the large fragment of DNA polymerase I (Klenow polymerase) was from New England Nuclear, Boston, MA; S1 nuclease and tRNA were from Sigma; AcA 34 column bed resin was from LKB, Gaithersburg, MD; EcoRI, EcoRI methylase and EcoRI linkers were from New England Biolabs, Beverly MA; RNAsin (ribonuclease inhibitor) was from Promega Biotech, Madison, Wisc. and all radioactive compounds were from Amersham, Arlington, Hts., IL.

The λgt10 vector (ATCC No. 40179) and associated E. coli cell lines were supplied by Thanh Huynh and Ronald Davis at Stanford University Medical School (see Huynh 1985). This vector has three important characteristics: (1) it has a unique EcoRI insertion site, which avoids the need to remove a center portion of DNA from the phage DNA before inserting new DNA; (2) DNA ranging in size from zero to about 8,000 bases can be cloned using this vector; and, (3) a library can be processed using E. coli MA150 cells (ATCC No. 53104) to remove clones which do not have DNA inserts.

(b) cDNA First Strand Synthesis

Poly-A mRNA was prepared as described in section D.(a) above, and resuspended in 50 mM Tris (pH 8.5), 10 mM $MgCl_2$, 4 mM DTT, 40 mM KCl, 500 µM of d(AGCT)TP, 10 µg/ml $dT_{12-18}$ primer, and 27.5 units/ml RNAsin. In a 120 µl reaction volume, 70 units reverse transcriptase were added per 5 µg of poly-A RNA. One reaction tube contained $\gamma$-$^{32}$P-dCTP (5 uCi/120 µl reaction) to allow monitoring of cDNA size and yield and to provide a first strand label to monitor later reactions. In order to disrupt mRNA secondary structure, mRNA in $H_2O$ was incubated at 70° C. for 3 min and the tube was chilled on ice. Reverse transcriptase was added and the cDNA synthesis was carried out at 42° C. for 60 min. The reaction was terminated by the addition of EDTA to 50 mM. cDNA yield was monitored by TCA precipitations of samples removed at the start of the reaction and after 60 min. Following cDNA synthesis, the cDNA existed as a cDNA-RNA hybrid. The cDNA-RNA hybrid was denatured by heating the mixture in a boiling water bath for 1.5 min, and cooled on ice.

(c) Second Strand DNA Synthesis

Single-stranded cDNA was allowed to self-prime for second strand synthesis. Both Klenow polymerase and reverse transcriptase were used to convert ss cDNA to ds cDNA. Klenow polymerase is employed first since its 3'-5' exonuclease repair function is believed to be able to digest non-flush DNA ends generated by self-priming and can then extend these flush ends with its polymerase activity. Reverse transcriptase is used in addition to Klenow polymerase, because reverse transcriptase is believed to be less likely to stop prematurely once it has bound to a template strand. The Klenow polymerase reaction was in a final 100 µl volume excluding enzyme. The reaction mix included 50 mM HEPES, pH 6.9, 10 mM $MgCl_2$, 50 mM KCl, 500 µM of each dNTP and cDNA. To begin the reaction, 20 to 40 units of Klenow polymerase (usually less than 5 µl) were added and the tubes incubated at 15° C. for 5 hrs. The reaction was terminated by the addition of EDTA to 50 mM. The mix was extracted with phenol and the nucleic acids were precipitated, centrifuged and dried.

The reverse transcriptase reaction to further extend the anti-complementary DNA strand was performed as described for the reaction to originally synthesize cDNA, except $dT_{10-18}$ primer and RNAsin were absent, and 32 units of reverse transcriptase were used in a 120 µl reaction. The reaction was terminated by the addition of EDTA to 50 mM. The mixture was extracted with an equal volume of phenol and the nucleic acid was precipitated, centrifuged and dried.

(d) S1 Nuclease Treatment

200 µl of 2×S1 buffer (1×S1 buffer is 30 mM sodium acetate, pH 4.4, 250 mM NaCl, 1 mM $ZnCl_2$), 175 µl of H₂O and 525 units of S1 nuclease were added to the tubes containing 125 μl of the second strand synthesis reaction product. The tubes were incubated at 37° C. for 30 min and the reaction was terminated by addition of EDTA to 50 mM. The mixture was extracted with an equal volume of phenol/chloroform (1:1). The aqueous phase was extracted with ethyl ether to remove residual phenol. The DNA was precipitated with ethanol and air dried.

(e) EcoRI Methylation Reaction

Since the ds cDNAs were copied from a large variety of mRNAs, many of the ds cDNAs probably contained internal EcoRI restriction sites. It was desired to protect such cleavage sites from EcoRI cleavage, to enable the use of blunt-ended EcoRI linkers which were subsequently cleaved with EcoRI to create cohesive overhangs at the termini.

In an effort to prevent the undesired cleavage of internal EcoRI sites, the ds cDNA was methylated using EcoRI methylase. DNA pellets were dissolved in 40 μl of 50 mM Tris pH 7.5, 1 mM EDTA, 5 mM DTT. Four μl of 100 uM S-adenosyl-L-methionine and 1 μl (80 units) of EcoRI methylase were added. Tubes were incubated at 37° C. for 15 min and then at 70° C. for 10 minutes to inactivate the methylase.

It was subsequently discovered that the methylation reaction described below was unsuccessful in preventing EcoRI cleavage at an internal site within the EPSP synthase coding region, apparently because of inactive methylase reagent. The cleavage of the internal EcoRI site required additional steps to isolate a full-length cDNA, as described below. To avoid those additional steps, the methylation reagents and reaction conditions should be used simultaneously on the cDNA and on control fragments of DNA, and protection of the control fragments should be confirmed by EcoRI digestion before digestion is performed on the cDNA.

(f) DNA Polymerase I Fill-In Reaction

To the tube containing 45 μl of cDNA (prepared as described above) were added 5 μl of 0.1 M MgCl₂, 5 μl of 0.2 mM d(ACGT)TP and 10 units of DNA polymerase I. The tube was incubated at room temperature for 10 min. The reaction was terminated by the addition of EDTA to 25 mM. One microgram of uncut γgt10 DNA was added as a carrier and the mix was extracted with phenol/chloroform (1:1). The nucleic acid in the mix was precipitated with ethanol, centrifuged and dried.

(g) Ligation of EcoRI Linkers to Methylated ds cDNA

Approximately 400 pmoles of EcoRI linkers (5'-CGGAATTCCG-3') were dissolved in 9 μl of 20 mM Tris, pH 8.0, 10 mM MgCl₂, 10 mM DTT containing 50 μCi of γ-³²P-ATP (5000 Ci/mmole) and 2 units of T4 polynucleotide kinase. The oligonucleotides were incubated at 37° C. for 30 minutes to allow them to anneal to each other, creating double-stranded, blunt-ended linkers. 2 units of T4 polynucleotide kinase and 1 μl of 10 mM ATP were added and incubated at 37° C. for an additional 30 min. The linkers were stored at −20° C. The methylated DNA pellet was resuspended in tubes containing 400 pmoles of the kinased linkers. Ligation of the EcoRI linkers to the methylated DNA was carried out by adding 1 μl of T4 ligase and incubating the reaction mixture at 12-14° C. for 2 days.

(g) Digestion with EcoRI to Create Cohesive Termini

To 11 μl of the reaction production from Section 1.E.(g) above, 10 ml of a solution containing 50 mM Tris, pH 7.5, 10 mM MgSO₄, 200 mM NaCl were added. T4 DNA ligase was heat inactivated by incubation at 70° C. for 10 min. Forty units of EcoRI were added and the incubation was carried out at 37° C. for 3 hr. The reaction was terminated by addition of EDTA to 50 mM. The sample was clarified by centrifugation and applied to an AcA 34 column.

(i) AcA 34 Column Chromatography

Free linkers (those not ligated to ds cDNA) were removed from ds cDNA with attached linkers, to prevent them from interfering with the insertion of the desired ds cDNAs into the cloning vectors. AcA 34 resin (a mixture of acrylamide and agarose beads, normally used for sizing) preswollen in 2 mM citrate buffer and 0.04% sodium azide in water, was added to the 1 ml mark of a 1 ml plastic syringe plugged with glass wool. The column was equilibrated with 10 mM Tris-HCl pH 7.5, 1 mM EDTA, 400 mM NaCl. The ds cDNA mixtures with ligated linkers and free linkers (~45 μl) was brought to 400 mM NaCl. 1 μl of 0.5% bromophenol blue dye (BPB) was added, and the sample was applied to the column which was run in equilibration buffer at room temperature. Ten 200 μl fractions were collected. The BPB dye normally eluted from the column in the sixth tube or later. Tubes 1 and 2 were combined and used as the source of ds cDNA for cloning.

(j) Assembly of λgt10 clones

The ds cDNA was mixed with 1 μg of EcoRI-cut λgt10 DNA, precipitated with ethanol, and centrifuged. After washing the pellet once with 70% ethanol, the DNA pellet was air dried and resuspended in 4.5 μl of 10 mM Tris-HCl pH 7.5, 10 mM MgCl₂, 50 mM NaCl. To anneal and ligate the cDNA inserts to the left and right arms of the λgt10 DNA, the mixture was heated at 70° C. for 3 min., then at 50° C. for 15 min. The mixture was chilled on ice and 0.5 μl each of 10 mM ATP, 0.1 M DTT, and sufficient T4 DNA ligase to ensure at least 90% completion were added. The reaction was incubated at 14° C. overnight, which allowed the insertion of the ds cDNA into the EcoRI site of the λgt10 DNA. The resulting DNA was packaged into phage particles vitro using the method described by Soherer 1981.

(k) Removal of Phages Without Inserts

Insertion of a cDNA into the EcoRI site of λgt10 results in inactivation of the C1 gene. λgt10 phages with inactivated C1 genes (i.e., with inserts) replicate normally in *E. coli* MA150 cells. By contrast, λgt10 phages without inserts are unable to replicate in the MA150 strain of *E. coli*. This provides a method of removing λgt10 clones which do not have inserts.

The phages in the library were first replicated in *E. coli* C600 (M+R−) cells which modified the λgt10 DNA to protect it from the *E. coli* MA150 restriction system. A relatively small number of *E. coli* C600 cells were infected and then plated with a 20 fold excess of MA150 (M+R+) cells. The primary infection thus occurred in the M+R− cells where all the phages will grow, but successive rounds of replication occurred in the MA150 cells which prevented the replication of phages without inserts. The amplified phage library was collected from the plates, and after removal of agar and other contaminants by centrifugation, the recombinant phages were ready to use in screening experiments.

F. Screening of cDNA Library; Selection of pMON9531

Approximately 600 phages (each plate) were spread on 10 cm×10 cm square plates of solid NZY agar (Maniatis 1982) with 0.7% agarose. A translucent lawn of *E. coli* MA150 cells were growing on the plates. Areas where the phages infected and killed the *E. coli* cells were indicated by clear areas called "plaques", which were visible against the lawn of bacteria after an overnight incubation of the plates at 37° C. Six plates were prepared in this manner. The plaques were pressed against pre-cut nitrocellulose filters for about 30 min. This formed a symmetrical replica of the plaques. To affix the phage DNA, the filters were treated with 0.5 M NaOH and 2.5 M NaCl for 5 min. The filters were then treated sequentially with 1.0 M Tris-HCl, pH 7.5 and 0.5 M Tris-HCl, pH 7.5 containing 2.5 M NaCl to neutralize the NaOH. They were then soaked in chloroform to remove bacterial debris. They were then air-dried and baked under a vacuum at 80° C. for 2 hours, and allowed to cool to room temperature. The filters were then hybridized with $^{32}$P-labelled EPSP-1 probe ($2 \times 10^6$ cpm/filter) as described in Section 1.D(e) above. After 48 hr of hybridization, the filters were washed in 6x SSC at room temperature twice for 20 min and then at 37° C. for 5 min. These washes removed non-specifically bound probe molecules, while probe molecules with the exact corresponding sequence (which was unknown at the time) remained bound to the phage DNA on the filter. The filters were analyzed by autoradiography after the final wash. After the first screening step, seven positively hybridizing signals appeared as black spots on the autoradiograms. These plaques were removed from the plates and replated on the fresh plates at a density of 100-200 plagues/plate. These plates were screened using the procedure described above. Four positively hybridizing phages were selected. DNA was isolated from each of these four clones and digested with EcoRI to determine the sizes of the cDNA inserts. The clone containing the largest cDNA insert, approximately 330 bp, was selected, and designated λE3. The cDNA insert from λE3 was inserted into plasmid pUC9 (Vieira 1981), and the resulting plasmid was designated pMON9531.

To provide confirmation that the pMON9531 clone contained the desired EPSP synthase sequence, the insert was removed from the pMON9531 clone by digestion with EcoRI. This DNA fragment was then sequenced by the chemical degradation method of Maxam (1977). The amino acid sequence deduced from the nucleotide sequence corresponded to the EPSP synthase partial amino acid sequence shown in Table 1.

G. Creation of λF7 Genomic DNA Clone

In order to obtain the entire EPSP synthase gene, chromosomal DNA from the MP4-G cells line was digested with BamHI and cloned into a phage vector to create a library, which was screened using the partial EPSP synthase sequence from pMON9531 as a probe.

(a) Preparation of MP4-G Chromosomal DNA Fragments

MP4-G cells were frozen and pulverized in a mortar with crushed glass in the presence of liquid nitrogen. The powdered cells were mixed with 8 ml/g of cold lysis buffer containing 8.0M urea, 0.35M NaCl, 0.05M Tris-HCl (pH 7.5), 0.02M EDTA, 2% sarkosyl and 5% phenol. The mixture was stirred with a glass rod to break up large clumps. An equal volume of a 3:1 mixture of phenol and chloroform containing 5% isoamyl alcohol was added. Sodium dodecyl sulfate (SDS) was added to a final concentration of 0.5%. The mixture was swirled on a rotating platform for 10-15 minutes at room temperature. The phases were separated by centrifugation at 6,000×g for 15 minutes. The phenol/chloroform extraction was repeated. Sodium acetate was added to the aqueous phase to a final concentration of 0.15 M and the DNA was precipitated with ethanol. The DNA was collected by centrifugation, dissolved in 1×TE (10mM Tris-HCl, pH 8.0, 1 mM EDTA) and banded in a CsCl-ethidium bromide gradient. The DNA was collected by puncturing the side of the tube with a 16 gauge needle. The ethidium bromide was extracted with CsCl-saturated isopropanol, and the DNA was dialyzed extensively against 1×TE. Approximately 400 μg of DNA was isolated from 12 g of cells.

MP4-G chromosomal DNA (10 μg) was digested to completion with 30 units of BamHI in a buffer containing 10 mM Tris, pH 7.8, 1 mM DTT, 10mM MgCl$_2$, 50 mM NaCl for 2 hours at 37° C. The DNA was extracted with phenol followed by extraction with chloroform and precipitated with ethanol. The DNA fragments were suspended in 1×TE at a concentration of 0.5 μg/μl.

(b) Cloning of MP4-G Chromosomal DNA Fragments in λMG14

DNA from phage λMG14 (obtained from Dr. Maynard Olson of the Washington University School of Medicine, St. Louis, MO) was prepared by the method described in Maniatis 1982. 150 μg of DNA was digested to completion with BamHI in a buffer containing 10mM Tris-HCl, pH 7.8, 1 mM DTT, 10 mM MgCl$_2$, 50 mM NaCl. The completion of the digest was checked by electrophoresis through 0.5% agarose gel. The phage DNA was then extracted twice with phenol-chloroform-isoamyl alcohol (25:24:1) and precipitated with ethanol. The DNA was resuspended in 1×TE at a concentration of 150 μg/ml. MgClz was added to 10 mM and incubated at 42° C. for 1 hr to allow the cohesive ends of λDNA to reanneal. Annealing was checked by agarose gel electrophoresis.

After annealing, DNA was layered over a 38 ml (10-40%, w/v) sucrose gradient in a Beckman SW27 ultracentrifuge tube. The gradient solutions were prepared in a buffer containing 1 M NaCl, 20 mM Tris-HCl (pH 8.0), 5 mM EDTA. 75 μg of DNA was loaded onto each gradient. The samples were centrifuged at 26,000 rpm for 24 hours at 15° C. in a Beckman SW 27 rotor. Fractions (0.5 ml) were collected from the top of the centrifuge tube and analyzed for the presence of DNA by gel electrophoresis. The fractions containing the annealed left and right arms of λDNA were pooled together, dialyzed against TE and ethanolprecipitated. The precipitate was washed with 70% ethanol and dried. The DNA was dissolved in TE at a concentration of 500 μg/ml.

The purified arms of the vector DNA and the BamHI fragments of MP4-G DNA were mixed at a molar ratio of 4:1 and 2:1 and ligated using T4 DNA ligase in a ligase buffer containing 66 mM Tris-HCl, pH 7.5,5 mM MgCl$_2$, 5 mM DTT and 1 mM ATP. Ligation was carried out overnight at 15° C. Ligation was checked by agarose gel eletrophoresis. Ligated phage DNA carrying inserts of MP4-G DNA were packaged into phage capsids in vitro using commercially available packaging extracts (Promega Biotech, Madison, WI). The packaged phage were plated in 10 cm×10 cm square plates of NZY agar in 0.7% agarose at a density of approximately 6000 plaques per plate using *E. coli* C600 cells. After overnight incubation at 37° C., the plaques had formed, and the plates were removed from the incubator and chilled at 4° C. for at least an hour. The agar plates were pressed against nitrocellulose filters for 30 minutes to transfer phages to the filters, and the phage DNA was affixed to the filters as described previously. Each filter was hybridized for 40 hours at 42° C. with approximately 1.0×10⁶ cpm/filter of the 330 bp cDNA insert isolated from the pMON9531 clone, which had been nick-translated, using the procedure described in Maniatis (1982). The specific activity of the probe was 2–3×10⁸ cpm/μg of DNA. Hybridization was carried out in a solution containing 50% formamide, 5x SSC, 5x Denhardt's solution, 200 μg/ml tRNA and 0.1% SDS. Filters were washed in 1×SSC, 0.2% SDS at 50° C. and autoradiographed. Several positive signals were observed, and matched with plaques on the corresponding plate. The selected plaques were lifts, suspended in SM buffer, and plated with NZY agar. The replica plate screening process was repeated at lower densities until all the plaques on the plates showed positive signals. One isolate was selected for further analysis and was designated as the λF7 phage clone.

H. Preparation of pMON9543 and pMON9556

The DNA from λF7 was digested (separately) with BamHI, BglII, EcoRI, and HindIII. The DNA was hybridized with a nick-translated EPSP synthase sequence from pMON9531 in a Southern blot procedure. This indicated that the complementary sequence from λF7 was on a 4.8 kb BglII fragment. This fragment was inserted into plasmid pUC9 (Vieira 1982), replicated, nick-translated, and used to probe the petunia cDNA library, using hybridization conditions as described in Section 1.(G), using 10⁶ cpm per filter. A cDNA clone with a sequence that bound to the λF7 sequence was identified, and designated as pMON9543.

DNA sequence analysis (Maxam 1977) indicated that pMON9543 did not contain the stop codon or the 3' non-translated region of the EPSP synthase gene. Therefore, the EPSP synthase sequence was removed from pMON9543, nick-translated, and used as a probe to screen the cDNA library. A clone which hybridized with the EPSP synthase sequence was identified and designated as pMON9556. DNA sequence analysis indicated that the insert in this clone contained the entire 3' region of the EPSP synthase gene, including a polyadenylated tail. The 5' EcoRI end of this insert matched the 3' EcoRI end of the EPSP synthase insert in pMON9531. An entire EPSP synthase coding sequence was created by ligating the EPSP synthase inserts from pMON9531 and pMON9556.

I. Preparation of pMON546 Vector with CaMV35-S/EPSP Synthase Gene

The EPSP synthase insert in pMON9531 was modified by site-directed mutagenesis (Zoller et al, 1983) using an M13 vector (Messing 1981 and 1982) to create a BglII site in the 5' non-translated region of the EPSP synthase gene. The modified EPSP synthase sequence was isolated by EcoRI and BglII digestion, and inserted into vector, pMON530, a binary vector for Agrobacterium-based plant transformation to obtain pMON536. The 1.62 kb EcoRI-EcoRI fragment from pMON9556 was then inserted into pMON536 to obtain pMON546. Since pMON530 already contained a 35S promoter from a cauliflower mosaic virus (CaMV) next to the BglII site, this created a chimeric CaMV35S/EPSP synthase gene in pMON546.

pMON530, a derivative of pMON505 carrying the 35S-NOS cassette, was prepared in the following manner: The CaMV35S promoter was isolated from the pOS-1 clone of CM4-184 as an AluI (n 7143)-EcoRI* (n 7517) fragment which was inserted first into pBR322 cleaved with BamHI, treated with Klenow fragment of DNA polymerase I and then cleaved with EcoRI. The promoter fragment was then excised from pBR322 with BamHI and EcoRI, treated with Klenow polymerase and inserted into the SmaI site of M13mp8 so that the EcoRI site of the mp8 multi-linker was at the 5' end of the promoter fragment. The nucleotide numbers refer to the sequence of CM1841 (Gardner et al., 1981). Site directed mutagenesis was then used to introduce a G at nucleotide 7464 to create a BglII site. The CaMV35S promoter fragment was then excised from the M13 as a 330 bp EcoRI-BglII fragment which contains the CaMV35S promoter, transcription initiation site and 30 nucleotides of the 5' non-translated leader but does not contain any of the CaMV translational initiators nor the CaMV35S transcript polyadenylation signal that is located 180 nucleotides downstream from the start of transcription (Covey et al., 1981; Guilley et al., 1982). The CaMV35S promoter fragment was joined to a synthetic multi-linker and the NOS 3' non-translated region and inserted into pMON200 (Fraley et al., 1985; Rogers et al., 1986) to give pMON316, see FIG. 3.

Plasmid pMON316 contains unique cleavage sites for BglII, ClaI, KpnI, XhoI and EcoRI located between the 5' leader and the NOS polyadenylation signals. Plasmid pMON316 retains all of the properties of pMON200. The complete sequence of the CaMV35S promoter, multi-linker and NOS 3' segment is given in FIG. 4. This sequence begins with the XmnI site created by Klenow polymerase treatment to remove the EcoRI site located at the 5' end of the CaMV35S promoter segment.

Figure 6:
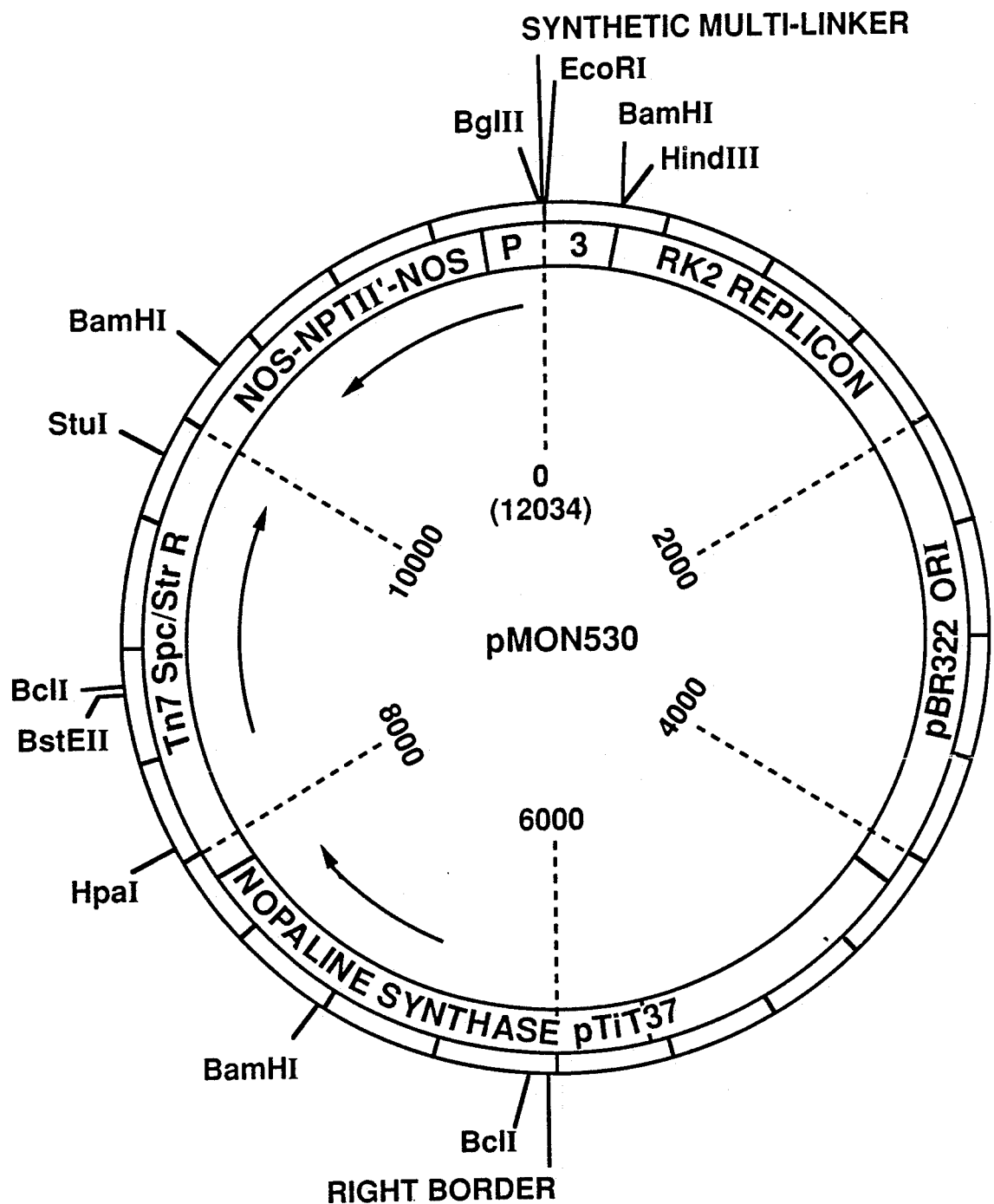
FIG. 6 shows a plasmid map for binary plant transformation vector pMON530.

Plasmid pMON530 (see FIG. 6) is a derivative of pMON505 prepared by transferring the 2.3 kb StuI-HindIII fragment of pMON316 into pMON526. Plasmid pMON526 is a simple derivative of pMON505 in which the SmaI site is removed by digestion with XmaI, treatment with Klenow polymerase and ligation. Plasmid pMON530 retains all the properties of pMON505 and the CaMV35S-NOS expression cassette and now contains a unique cleavage site for SmaI between the promoter and polyadenylation signal.

Binary vector pMON505 is a derivative of pMON200 in which the Ti plasmid homology region, L1H, has been replaced with a 3.8 kb HindIII to SmaI segment of the mini RK2 plasmid, pTJS75 (Schmidhauser & Helinski, 1985). This segment contains the RK2 origin of replication, oriV, and the origin of transfer, oriT, for conjugation into using the tri-parental mating procedure (Horsch Klee, 1986).

Figure 5:
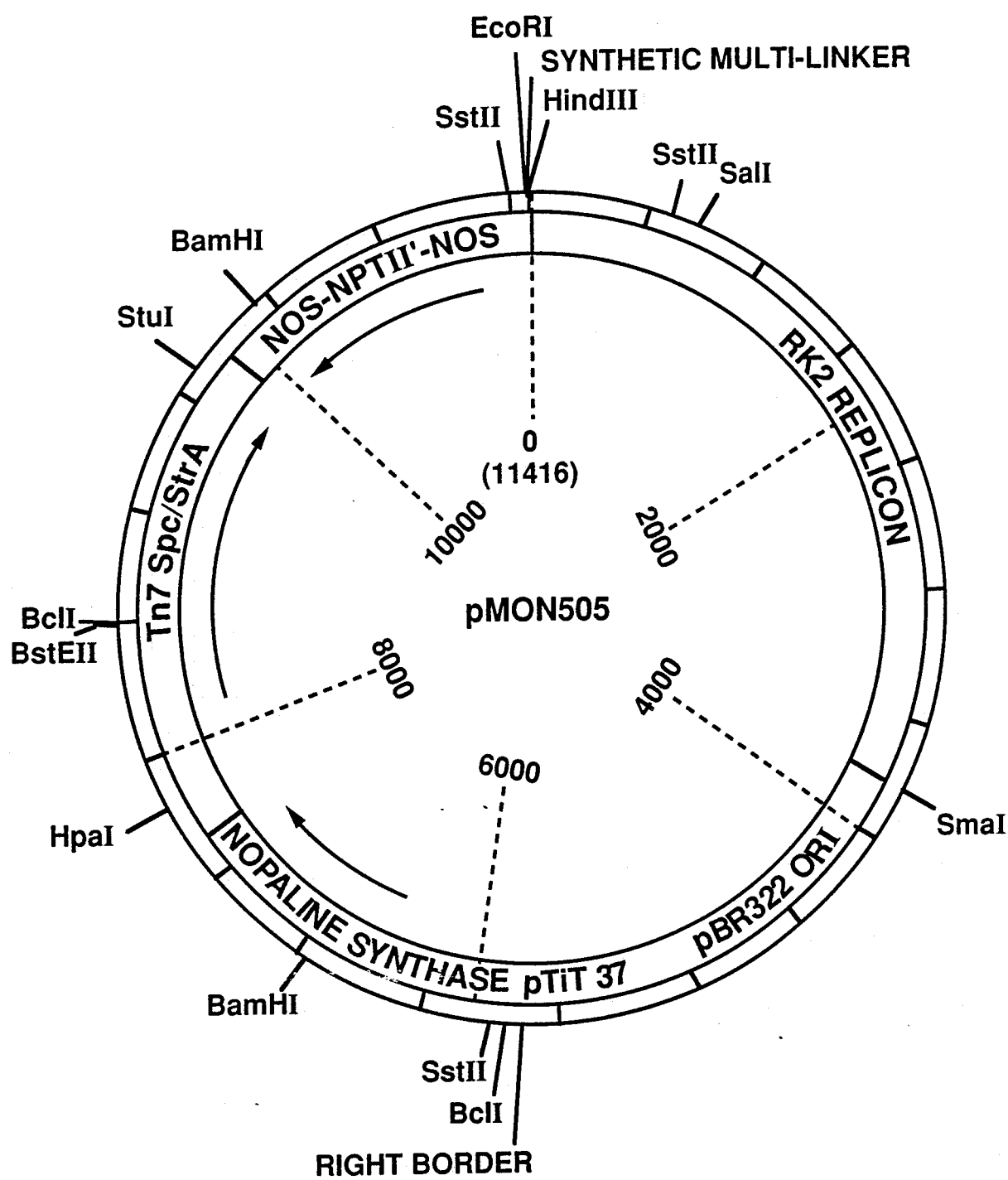
FIG. 5 shows a plasmid map for binary plant transformation vector pMON505.

Referring to FIG. 5, plasmid pMON505 retains all the important features of pMON200 including the synthetic multi-linker for insertion of desired DNA fragments, the chimeric NOS-NPTII'NOS gene for kanamycin resistance determinant for selection of E. coli and A. tumefaciens, an intact nopaline synthase gene for facile scoring of transformants and inheritance in progeny and a pBR322 origin of replication for ease in making large amounts of the vector in E. coli. Plasmid pMON505 contains a single T-DNA border derived from the right end of the pTiT37 nopaline-type T-DNA. Southern analyses have shown that plasmid pMON505 and any DNA that it carries are integrated into the plant genome, that is, the entire plasmid is the T-DNA that is inserted into the plant genome. One end of the integrated DNA is located between the right border sequence and the nopaline synthase gene and the other end is between the border sequence and the pBR322 sequences.

Plasmid pMON546 contained (1) the CaMV35-S/EPSP synthase gene; (2) a selectable marker gene for kanamycin resistance (Kan$^R$); (3) a nopaline synthase (NOS) gene as a scorable marker; and (4) a right T-DNA border, which effectively caused the entire plasmid to be treated as a "transfer DNA" (T-DNA) region by *A. tumefaciens* cells.

This plasmid was inserted into *A. tumefaciens* cells which contained a helper plasmid, pGV3111-SE. The helper plasmid encodes certain enzymes which are necessary to cause DNA from pMON546 to be inserted into plant cell chromosomes. It also contains a kanamycin resistance gene which functions in bacteria.

A culture of *A. tumefaciens* containing pMON546 and pGV3111-SE was deposited with the American Type Culture Collection (ATCC) and was assigned ATCC accession number 53213. If desired, either one of these plasmids may be isolated from this culture of cells using standard methodology. For example, these cells may be cultured with *E. coli* cells which contain a mobilization plasmid, such as pRK2013 (Ditta 1980). Cells which become Spc/Str$^R$, Kan$^S$ will contain pMON546, while cells which become Kan$^R$, Spc/Str$^S$ will contain pGV3111-SE.

GLYPHOSATE-TOLERANT PETUNIA PLANTS

Leaf disks with diameters of 6 mm (¼ inch) were taken from surface-sterilized petunia leaves. They were cultivated on MS104 agar medium for 2 days to promote partial cell wall formation at the wound surfaces. They were then submerged in a culture of *A. tumefaciens* cells containing both pMON546 and GV3111-SE which had been grown overnight in Luria broth at 28° C., and shaken gently. The cells were removed from the bacterial suspension, blotted dry, and incubated upside down on filter paper placed over "nurse" cultures of tobacco cells, as described in Horsch (1980). After 2 or 3 days, the disks were transferred to petri dishes containing MS media with 500 μg/ml carbenicillin and 0. 0.1, 0.25, or 0.5 mM glyphosate (sodium salt), with no nurse cultures.

Control tissue was created using *A. tumefaciens* cells containing the helper plasmid pGV3111-SE and a different plant transformation vector, pMON505, which contained a T-DNA region with a NOS/NPTII/NOS kanamycin resistance gene and a NOS selectable marker gene identical to pMON546, but without the CaMV35S/EPSP synthase gene.

Within 10 days after transfer to the media containing glyphosate, actively growing callus tissue appeared on the periphery of all disks on the control plate containing no glyphosate. On media containing 0.1 mM glyphosate, there was little detectable difference between the control disks and the transformed tissue. At 0.25 mM glyphosate, there was very little growth of callus from control disks, while substantial growth of transformed tissue occurred. At 0.5 mM glyphosate, there was no callus growth from the control disks, while a significant number of calli grew from the transformed disks. This confirms that the CaMV35S/EPSP synthase gene conferred glyphosate resistance upon the transformed cells.

Transformed petunia plants were produced by regeneration from the above-described transformed leaf disks by the procedure described in Horsch et al (1985). The transformed plants obtained contained the pMON546 vector, described hereinabove, which contains the CaMV 35S promoter fused to the wild-type- petunia EPSP synthase gene.

Four individual representative transgenic seedlings were selected, grown and tested in the testing procedure described below, along with four individual non-transformed (wild-type) petunia seedlings.

The plants were grown in a growth medium in a growth chamber at 26° C. with 12 hours of light per day. The plants were fertilized weekly with a soluble fertilizer and watered as needed. The plants were sprayed at a uniform and reproducible delivery rate of herbicide by use of an automated track sprayer. The glyphosate solution used was measured as pounds of glyphosate acid equivalents per acre, mixed as the glyphosate isopropylamine salt, with an ionic surfactant.

Four individual wild-type (non-transformed) petunia plants were selected for use as control plants. Four individual transformed plants containing the pMON546 vector were selected by kanamycin resistance as described in Horsch et al (1985).

The control plants and the transformed plants were sprayed with the isopropylamine salt of glyphosate at the application level listed in Table 2 below; the experimental results obtained are also summarized in Table 2.

TABLE 2

| | Plant Response to Glyphosate Spraying | |
|---|---|---|
| Plant Type | Glyphosate Dose* | Visual Appearance |
| Control[1] | 0.8 #/acre | completely dead, plants showed very rapid chlorosis and bleaching, wilted and died |
| Chimeric EPSP synthase | 0.8 #/acre | growing well, slight chlorosis in new leaves which are growing with normal morphology, plants appear healthy and started to flower |

*Acid Equivalent
[1]wild-type plant or transformed with control vector (pMON505)

As indicated in Table 2, the control plants were killed when sprayed with 0.8 pounds/acre of glyphosate. In contrast, the petunia plants which were transformed were healthy and viable after spraying with 0.8 pounds/acre. The transformed plants are more resistant to glyphosate exposure than the non-transformed control plants.

Glyphosate-Tolerant Petunia EPSP Synthase

A plant transformation vector carrying a glyphosate-tolerant petunia EPSP synthase mutant was prepared in the following manner.

Plasmid pMON342 carries the "mature" wildtype petunia EPSP synthase coding sequence (without chloroplast transmit peptide) expressed from the double phage lambda pL promoter. This plasmid is derived from pMON9544 and pMON9556.

In order to introduce a unique NcoI site and ATG translational initiation signal in the wildtype petunia EPSP synthase cDNA just outside the coding sequence for the mature protein and at the same time remove the chloroplast transit peptide coding sequence, M8017 (the M13mp9 clone of the 300 bp EcoRI cDNA fragment) was subjected to site directed mutagenesis using the procedure of Zoller and Smith (1983) and the following mutagenesis primer:

5'-ATCTCAGAAGGCTCCATGGTGCT-
GTAGCCA-3'

A mutant phage clone was isolated that contained a NcoI site. The presence of the above-described mutation was confirmed by sequence analysis. This M13mp9 clone was designated M8019.

Plasmid pMON6001 is a derivative of pBR327 (Soberon et al., 1980) carrying the *E. coli* K12 EPSP synthase coding sequence expressed from two tandem copies of a synthetic phage lambda pL promoter. Plasmid pMON6001 was constructed in the following manner. First, pMON4 (Rogers et al., 1983) was digested with ClaI and the 2.5 kb fragment was inserted into a pBR327 that has also been cleaved with ClaI. The resulting plasmid, pMON8, contains the EPSP synthase coding sequence reading in the same direction as the beta-lactamase gene of pBR327.

To construct pMON25, a derivative of pMON8 with unique restriction endonuclease sites located adjacent to the *E. coli* EPSP synthase coding sequence, the following steps were taken. A deletion derivative of pMON4 was made by cleavage with BstEII and religation. The resultant plasmid pMON7 lacks the 2 kb BstEII fragment of pMON4. Next, a 150 bp HinfI to NdeI fragment which encodes the 5' end of the EPSP synthase open reading frame was isolated after digestion of pMON7 with NdeI and HinfI and electroelution following electrophoretic separation on an acrylamide gel. This piece was added to the purified 4.5 kb BamHI-NdeI fragment of pMON8 which contains the 3' portion of the EPSP synthase coding sequence and a synthetic linker with the sequence:

5'-GATCCAGATCTGTTGTAAGGAGTCTAGACCATGG-3'
3'-GTCTAGACAACATTCCTCAGATCTGGTACCTTA-5'

The resulting plasmid pMON25 contains the EPSP synthase coding sequence preceded by unique BamHI and BglII sites, a synthetic ribosome binding site, and unique XbaI and NcoI sites the latter of which contains the ATG translation initiator signal of the coding sequence.

To construct pMON6001, pMON25 was digested with BamHI and mixed with a synthetic DNA fragment containing a partial phage lambda pL sequence (Adams and Galluppi, 1986) containing BamHI sticky ends:

5'-GATCCTATCTCTGGCGGTGTTGACATAAATACCACTGGCGGTGATACTGAGCACATCG-3'
3'-GATAGAGACCGCCACAACTGTATTTATGGTGACCGCCACTATGACTCGTGTAGCCTAG-5'

The resulting plasmid pMON6001 carries two copies of the synthetic phage lambda pL promoter fragments as direct repeats in the site of pMON25 in the correct orientation to promote transcription of the EPSP synthase coding sequence.

Plasmid pMON6001 was cleaved with NcoI and EcoRI and the 3 kb fragment isolated from an agarose gel. This fragment was mixed with the small 100 bp NcoI-EcoRI fragment purified from M8019. Following ligation and transformation a clone was identified that contained the small 100 bp NcoI-EcoRI fragment corresponding to the 5' end of the "mature" EPSP synthase of petunia. This construct was designated pMON9544.

Plasmid pMON9544 was digested with EcoRI and treated with alkaline phosphatase. The EcoRI fragment of pMON9544 was mixed with pMON9556 DNA that had been cleaved with EcoRI to release a 1.4 kb fragment encoding the 3' portion of the petunia EPSP synthase coding sequence. Following ligation and transformation, a clone was identified that could complement an *E. coli* aroA mutation and carried the 1.4 kb fragment of pMON9556. This plasmid was designated pMON342.

The EcoRI site at the 3' end of the EPSP synthase in pMON342 was replaced with a ClaI site to facilitate construction. This was accomplished by partial digestion with EcoRI followed by digestion with mungbean nuclease to make the ends blunt. ClaI linkers (5'-CATCGATG-3', New England Biolabs) were added to the blunt ends by ligation with T4 DNA ligase. The mixture was digested with ClaI to produce sticky ends, and the 5 kb EcoRI partial digest was isolated from an agarose gel and ligated with T4 DNA ligase. This plasmid was designated pMON9563.

A 29-nucleotide mutagenic deoxyoligonucleotide having the following sequence:

5'-GCCGCATTGCTGTAGCTGCATTT-
CCAAGG-3' was synthesized for introducing the alanine for glycine substitution at position 101 using an automated DNA synthesizer (Applied Biosystems, Inc.). The deoxyoligonucleotide was purified by preparative polyacrylamide gel electrophoresis.

The 770 bp EcoRI-HindIII fragment of pMON9563 was subcloned into a EcoRI-HindIII digested M13mp10 bacteriophage vector (New England Biolabs). The single-stranded template DNA was prepared from the subclone as described in the M13 cloning and sequencing handbook by Amersham, Inc. (Arlington Heights, IL.).

Oligonucleotide mutagenesis reactions were performed as described by Zoller and Smith (1983). Single-stranded M13mp10 template DNA (0.5 picamoles, pmole) containing the 770 bp EcoRI-HindIII fragment of the pMON9563 clone was mixed with 20 pmole of the above-described 29-mer deoxyoligonucleotide and 1 µl of 10×buffer DTT, pH 7.5) in a total volume of 10 µl. This mixture was heated at 70° C. for 5 minutes, placed at room temperature (23° C.) for 20 minutes and then placed on ice for 20 minutes. During the annealing reaction, the enzyme/nucleotide solution was prepared by addition of the following components: 1 µl of 10×buffer B (0.2M Tris-HCl, 0.1M MgCl₂, 0.1M DTT, pH 7.5), 1 µl each of 10 mM dNTPs, 1 µl of 10 mM rATP, 3 units of T4 DNA ligase, 2 units of the large fragment of DNA polymerase I and H₂O to a total volume of 10 µl. This solution was kept on ice until used.

After 20 minutes incubation on ice, 10 µl of the enzyme/nucleotide solution was added to the annealed DNA, mixed and maintained at 15° C. overnight. Three units of T4 DNA ligase were added again to ensure completion of the extension reaction to yield closed circular DNA molecules. This construct was designated M9551. The 770 bp EcoRI-HindIII fragment of M9551 was inserted into pMON9563 between the EcoRI and HindIII sites, replacing the corresponding wildtype fragment. This plasmid was designated pMON9566.

Plasmid pMON530 DNA was digested with BglII and ClaI, to which was added the 330 bp BglII-EcoRI EPSP synthase 3' fragment from pMON536 and purified 1.4 kb EcoRI-ClaI EPSP synthase 5' fragment from pMON9566 and then treated with T4 DNA ligase. Following transformation a plasmid was isolated that carried the intact mutant EPSP synthase coding sequence of petunia (with the coding sequence for the chloroplast transmit peptide) adjacent to the CaMV35S promoter. This plasmid was designated pMON567. Plasmid pMON567 was inserted into *A. tumefaciens* cells that contained helper plasmid pGV3111-SE.

A culture of *A. tumefaciens* cells containing pMON567/pGV3111-SE was contacted with leaf disks taken from tobacco plants (*Nicotiana tobacam* CV H425) as described by Horsch (1985). The *Agrobacterium* cells inserted the mutant EPSP synthase gene into the chromosomes of the plant cells. Plant cells resistant to kanamycin were selected and regenerated into differentiated plants by the procedure of Horsch (1985).

Progeny of these plants were propagated and grown to a rosette diameter of about 10 cm corresponding to a plant age of about four weeks. The plants were sprayed with glyphosate at levels corresponding to 2.0 and 3.6 pounds acid equiv./acre. The effect of glyphosate on the transformed plants was scored at 7 and 14 days. The effect was translated to a numerical scale of 0–10 in which 0 represents total kill and 10 is the normal, unsprayed plant. The data below demonstrates that tobacco plants transformed with the glyphosate-tolerant EPSP synthase gene of petunia exhibit substantial tolerance even to these high levels of glyphosate. The values represent the best transformant for both wild-type EPSP synthase and glyphosate-tolerant EPSP synthase genes.

TABLE 3

| | Relative Effect of Glyphosate[1] | | | | | |
| | pounds/Acre | | | | | |
| | 0.4 | | 2.0 | | 3.6 | |
| Day | GT[2] | WT[3] | GT | WT | GT | WT |
|---|---|---|---|---|---|---|
| 7 | 8.0 | 6.0 | 8.0 | 5.0 | 5.0 | 5.0 |
| 14 | 8.0 | 7.0 | 8.3 | 1.8 | 7.4 | 1.7 |
| 28 | 9.0 | 9.0 | 7.0 | 0.8 | 7.0 | 0.8 |

[1]0 represents total kill and 10 represents no effect.
[2]Glyphosate-tolerant petunia EPSP synthase.
[3]Wild-type EPSP synthase.

II. EPSP SYNTHASE OF TOMATO

Complementary DNA (cDNA) libraries were prepared from poly-A plus RNA isolated from mature tomato pistils or anthers by a modification of the methods of Huynh et al. (1985) and Gubler et al. (1983) as follows:

First Strand Synthesis

Quantities given below are those used to prepare the mature pistil cDNA library, the anther cDNA library was prepared in a similar manner.

10 μl of 400 μg/ml Actinomycin D (Sigma Chemical) in 50% ethanol was dried down in each reaction tube in a Savant speed vacuum. The following reagents were added to this tube (the reagents were added in the order given):

| Vol. | Substance | Final Conc/Amount |
|---|---|---|
| 62 μl | Autoclaved water | to final 100 μl |
| 10 μl | 10 X first strand buffer | see below |
| 10 μl | 5 mM dNTP | 500 μM each A,C,G,T[1] |
| 10 μl | 100 μg/ml oligo d(pT) | 1 μg[2] |
| 2 μl | RNAsin (30 U/μl) | 60 U[3] |
| 2 μl | RNA | ~1.5 μg |
| 3 μl | Reverse Transcriptase | 40 units[4] |
| 2 μl | 32P-dATP | 200 Ci/mMole[5] |

[1]Sigma Chemical, St. Louis, MO.
[2]Collaborative Research, Lexington, MA.
[3]Promega Biotech, Madison, WI.
[4]Life Sciences, St. Petersburg, FL.
[5]Amersham, Arlington Heights, IL.

The reaction mixture was incubated at 42° C. for 60 min. The reaction mixture was frozen on dry ice and stored at −20° C.

The quantity of cDNA synthesized was determined to be ~1.31 μg by precipitation of a portion of the reaction with trichloroacetic acid and scintillation counting.

Purification of First Strand

Biogel P60 (100-200 mesh, Bio Rad, Richmond, CA), pre-swollen in 10 mM Tris-HCl/1 mM EDTA, pH 8.0, (TE) was used to pour a column in a siliconed pasteur pipet plugged with siliconized glass wool (bed volume = 1 ml). The column was washed with several volumes of 1 mM Tris pH 7.6/ 0.01 mM EDTA. The column was calibrated by running 90 μl of this same solution plus 10 μl of column marker buffer (see below) over the column. The void volume was determined by the fraction containing the blue dye. More buffer was added to the column to elute the red dye.

The first strand reaction was extracted twice with an equal volume of phenol. 0.5 μl 2% bromophenol blue was added to the cDNA and it was loaded on the column, and the void volume was collected.

Column Marker Buffer:

5% Blue Dextrans (2 M dalton, Sigma)
0.05% Phenol Red (or Bromophenol blue at 0.1%) dissolved in 20 mM Tris pH 7-8/ 1 mM EDT Second Strand Synthesis and Methylation The first strand was dried to ca. 10 μl in a Savant speed vacuum.

| Vol. | Substance | First Conc./Amount |
|---|---|---|
| 3.8 μl | cDNA | ~500 ng of first strand |
| 10 μl | 10X Sec. Strand Buffer | 1 X |
| 0.8 μl | 5 mM dNTP | 40 μM each |
| 81.5 μl | Water | to 100 μl final volume |
| 2 μl | DNA Pol I (NEB) | 20 U |
| 0.4 μl | *E. coli* DNA ligase (NEB) | 2 U |
| 0.5 μl | RNAase H (BRL) | 1 U |
| 3 μl | 32P dCTP | 30 uCi |
| 1 μl | BSA (1:10 dil of BRL) | 50 μg/ml |

NEB = New England Biolabs, Beverly, MA
BRL = Bethesda Research Labs, Gaithersberg, MD The reaction was incubated at 14° C. for 60 min. then at room temperature for 60 min.

The following was added:

0.5 μl 5mM dNTP
1 μl T4 DNA polymerase (NEB)

The reaction was incubated for 30 min. at room temperature.

The following were added:

| 1.2 μl | mM S-adenosyl L-methionine (Sigma) | 12 μM |
| 1.0 μl | EcoRI Methylase (NEB) | 20 U |
| 2.4 μl | 0.5 M EDTA | 12 mM |

5 μl was removed from the reaction and added to 260 ng wild type lambda DNA (NEB) as control for methylation.

The reactions were incubated at 37° C. for 45 min.

Both the main and test reactions were heated to 68° C. for 10 min. to inactivate enzymes.

Measurements of trichloroacetic acid insoluble counts indicated that ~500 ng of ds cDNA (double stranded cDNA) was produced in the reaction.

| 10X Second Strand Buffer: | | |
| --- | --- | --- |
| 200 mM | Tris-HCl pH 7.4–7.5 | 1 M stock |
| 50 mM | MgCl$_2$ | 1 M stock |
| 1.0 M | KCl | 4 M stock |
| 100 mM | Ammonium sulfate | 1 M stock |
| 1.5 mM | Beta-NAD | 150 mM stock |

Assay for Completeness of Methylation

The following was added to the heat treated test methylation:

2 μl 100 mM Tris-HCl pH 7.6/100 mM MgCl$_2$/1.0 M NaCl
12 μl water
1 μl EcoRI (20 units BRL)
0.5 μl pUC19 (0.5 μg, NEB)

The reaction was incubated for 1 hr. at 37° C.

The products were run on an agarose minigel with undigested pUC19, and lambda digested with EcoRI and HindIII as size markers. The pUC19 in the reaction digested to completion indicating that the EcoRI was working efficiently, the lambda DNA was completely undigested showing that it had been protected by the methylation reaction. This shows that the methylase was effective in blocking the EcoRI sites in the cDNA from digestion.

ds cDNA Clean Up

The second strand reaction mixture was extracted twice with an equal volume of phenol, run over a P-60 column as described above and the void volume was collected and lyophilized in a Savant speed vacuum. The cDNA was dissolved in 3 μl 1 mM Tris-HCl pH 7.5/0.01 mM EDTA.

Ligation of Linkers to cDNA

The following was mixed in a microfuge tube:

3 μl ds cDNA (500 ng)
2.5 μl Phosphorylated EcoRI linkers (NEB, 250 ng)
1 μl 10×Ligation buffer
1 μl 10 mM ATP
1.5 μl water (for final vol of 10 μl )
1 μl T4 DNA Ligase (~400 units NEB)

The reaction was incubated at 14° C. for 12 hr.

10×Ligation Buffer
300 mM Tris-HCl pH 7.6
100 mM MgCl$_2$
50 mM DTT

Removal of Linkers

The following reagents were added:
2 μl 100 mM Tris-HCl pH 7.6/100 mM MgCl$_2$/1.0M NaCl
6 μl water The reaction was heated to 68° C. for 10 min. to inactivate ligase.

The following reagent was added:
2 μl EcoRI (40 units, NEB)

The reaction wa incubated at 37° C. for 2.5 hr.

The reaction was heated to 68° C. for 10 min. to inactivate EcoRI.

Size Cut cDNA and Separate From Linkers

5 μl of loading buffer was added to the digested cDNA/EcoRI linker reaction. The sample was electrophoresed on a 0.8% Sea Plaque agarose (FMC Corp., Rockland, MD)/TEA (40 mM Tris-Acetate pH 8.2/1.6 mM EDTA) minigel containing 0.3 μg/ml ethidium bromide. The gel was run at 4 V/cm until the bromophenol blue dye had migrated 4 cm. Lambda DNA digested with HindIII and EcoRI was used as a size marker. The markers were visualized by UV fluorescence, and a fragment of gel containing cDNA ranging in size from ~600 bp to greater than 10 kb was removed.

Loading Buffer:
250 mM EDTA pH 7
0.2% Bromophenol blue
50% Glycerol

Purification, Ligation and Packaging

The volume of the gel slice was determined to be ~500 μl by weighing and assuming a density of 1.0 g/ml. 140 μl of 20 mM Tris-HCl (pH 7.5)/200 mM NaCl/1.0 mM EDTA, and 20 μl of 5 M NaCl were added to the gel fragment. The mixture was heated to 68° C. for 15 min. and extracted twice with 500 μl of phenol. The DNA was purified from contaminants by chromatography on an EluTip D column (Schleicher & Schuell, Keen, NH) according to the manufacturers instructions. The final volume was 450 μl. The amount of radioactivity in the sample was determined by scintillation counting of an aliquot, and it was determined that 70 ng of cDNA was contained in the eluted volume.

2 μl (2 ug) lambda gt 10 arms (Vector Cloning Systems, San Diego, CA) were added to the cDNA followed by the addition of 2 volumes of cold ethanol. The sample was chilled to −80° C. for 15 min. and the precipitate was pelleted in a microfuge for 15 min. The tube was drained and rinsed with 200 μl of −20° C. 70% ethanol with caution so as not to disturb the pellet. The pellet was air dried for 30 min.

The following was added:
7.2 μl Water
1 μl 10 X Ligation buffer
1 μl ATP
0.8 μl T4 DNA ligase The reaction was incubated for 20 hrs at 14° C.

10 x Ligation Buffer
200 mM Tris-HCl pH 7.6
100 mM MgCl$_2$
50 mM Dithiothreitol (DTT)

One fourth (2.5 μl ) of the ligation reaction was packaged in vitro into phage using Gigapack packaging extracts (Stratagene Cloning Systems, San Diego, CA) according to the manufacturers instructions. Subsequent plating of the phage showed that this reaction contained $10^6$ recombinant plaque forming units (PFU). Packaging of the entire ligation mix would therefore produce $4 \times 10^6$ PFU. The remainder of the ligation mix was stored at −20° C. for future use.

Figure 7:
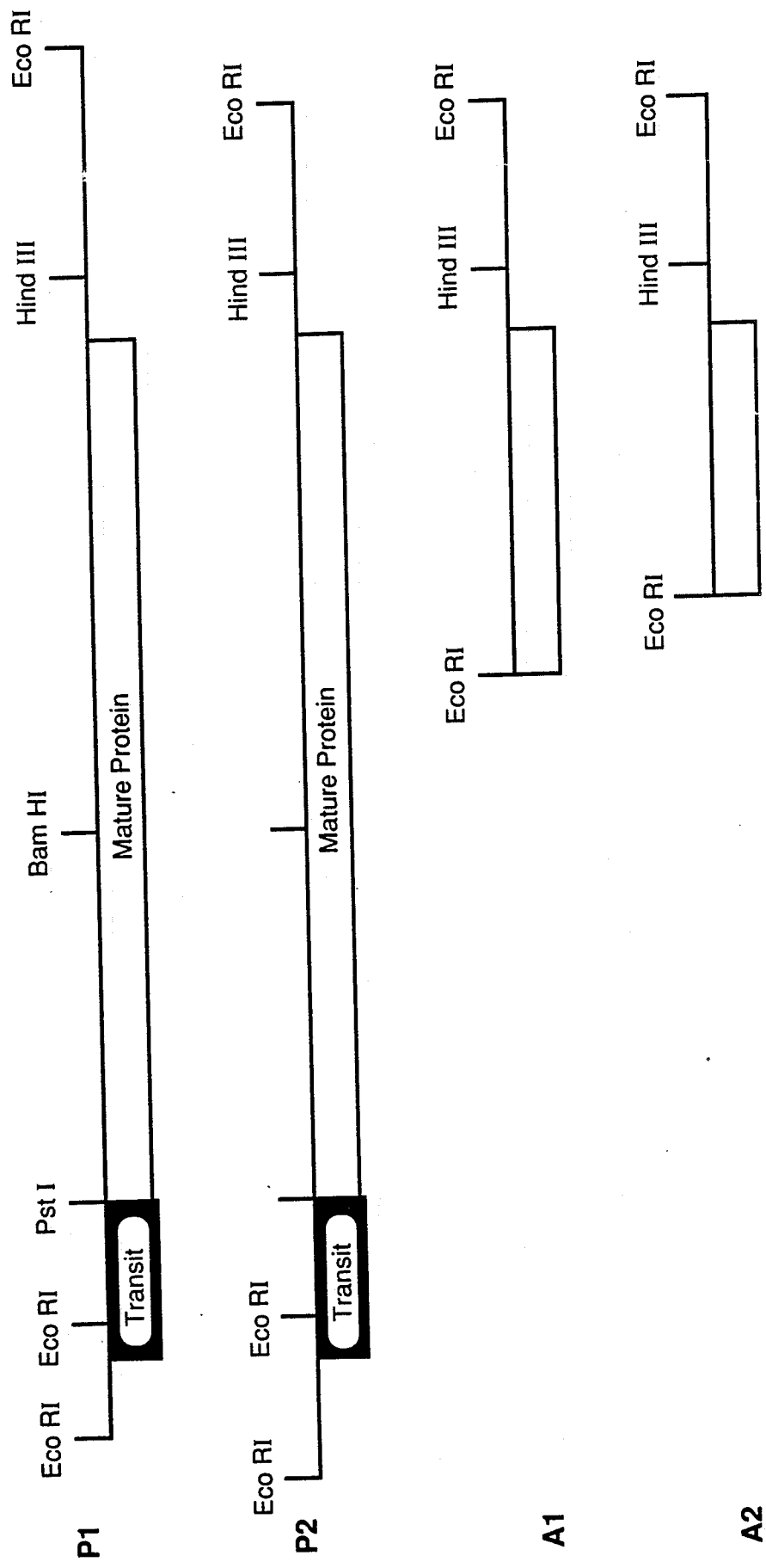
FIG. 7 shows a diagrammatic representation of the pistil and anther cDNA clones of tomato EPSP synthase.

Plaque lifts from the two libraries were screened with a $^{32}$P-labeled fragment from pMON6145 containing the complete coding sequence of petunia EPSP synthase.

pMON6145 is a derivative of plasmid pGEM2 (Promega Biotech, Madison, WI) described in the above-referenced and incorporated application S.N. 879,814, which carries a full-length cDNA clone of petunia EPSP synthase. Two hybridizing plaque were isolated from each library. Maps of the inserts of these phages are shown in FIG. 7. The large EcoRI fragments of the two pistil clones (P1 and P2) were subcloned into pUC19 (New England Biolabs), and the small EcoRI fragments were cloned into pUC119 forming plasmids 9591, 9589, 9595 and 9596, respectively.

pUC119 is constructed by isolating the 476 bp Hgi AI/Dra fragment of bacteriophage M13 and making the ends of the fragment blunt with T4 DNA polymerase (New England Biolabs). This fragment is then inserted into pUC19 (Yanisch-Perron et al., 1985) that has been digested with Nde I and filled in with Klenow DNA polymerase (New England Biolabs). The resulting plasmid (pUC119) can be used to produce single stranded DNA if cells harboring the plasmid are infected with a defective phage such as R408 (Stratagene Cloning Systems).

In order to introduce an NcoI site and an ATG translational initiation codon at the site predicted to be the start of the mature enzyme for in vitro expression in *E. coli*, the 1.6 kb EcoRI/HindIII fragment of pMON9591 was cloned into EcoRI/HindIII digested M13mp18 (New England Biolabs) producing a phage designated M9568. This clone was mutagenized with the oligonucleotide:

5'-AGCACAATCTCATGGGGTT-CCATGGTCTGCAGTAGCC-3' as previously described. Sequencing confirmed the success of the mutagenesis and the resulting phage was designated M9575. The 1.6 kb EcoRI/HindIII fragment of this phage was inserted into EcoRI/HindIII digested pMON6140. This plasmid was designated pMON9717. Plasmid pMON6140 is a derivative of pGEM1 (Promega Biotech, Madison, WI) which carries the same full-length cDNA clone of petunia EPSP synthase as described above for pMON6145.

In vitro transcription and translation of pMON9717 failed to produce an active enzyme. Subsequent sequencing of the cDNA from which this clone was prepared (pMON9591) revealed a single nucleotide deletion in the coding sequence which would result in a frame shift in the coding sequence. The region containing this deletion was replaced by the corresponding region from pMON9589 by exchanging the 900 bp BamHI/HindIII fragment of pMON9717 with the corresponding fragment of pMON9589. This plasmid was designated pMON9718. In vitro analysis of pMON9718 showed it coded for active tomato EPSP synthase.

A vector for high level expression in *E. coli* was constructed to further characterize the tomato EPSP synthase. The NcoI/HindIII fragment of pMON9718 containing the coding sequence for tomato EPSP synthase was inserted into NcoI/HindIII digested pMON5521. This placed the tomato EPSP synthase coding sequence under the control of the *E. coli* RecA promoter (Horii et al., 1980; Sancar et al., 1980). This plasmid was designated pMON9719. Plasmid pMON9719 was able to complement the EPSP synthase deficiency of an *E. coli* aroA mutant (SR481) demonstrating the synthesis of active EPSP synthase.

To introduce the alanine for glycine substitution at position 101 of the mature tomato EPSP synthase, the wild-type EPSP synthase coding sequence in phage M9568 was mutagenized with the oligonucleotide

5'-GCCGCATTGCTGTAGCTGCATTT-CCAAGG-3' by the method of Zoller and Smith (1983) as described previously. The phage was then mutagenized with the oligonucleotide

5'-AGCACAATCTCATGGGGTT-CCATGGTCTGCAGTAGCC-3' to introduce an NcoI site and translational initiation codon as previously described. The resulting construct was designated M9580. The EcoRI/BamHI fragment of M9580 which contains the region which had been mutagenized was inserted into pMON9718 which had been digested with EcoRI and BamHI. This plasmid was designated pMON9728. For expression in *E. coli* the NcoI/HindIII fragment of pMON9728 was inserted into NcoI/HindIII digested pMON5521 (described above) producing a plasmid which was designated pMON9729. Hence, plasmids pMON9719 and pMON9729 are similar plasmids in which the wild-type EPSP synthase and glyphosate-tolerant EPSP synthase (gly(101)-ala) of tomato are under the control of the recA promoter of *E. coli*. *E. coli* SR481 cells harboring pMON9719 or pMON9729 were grown under conditions which induce the expression of the RecA promoter. The cells were lysed and the extracts were assayed for EPSP synthase activity.

Specifically, the bacterial cell paste was washed twice with 0.9% saline, suspended in buffer (100 mM Tris-HCl, 5 mM dithiothreitol, 1 mM EDTA, 10% glycerol and 1 mM benzamidine HCl) passed twice through the French Pressure Cell at 1000 psi. The cell extract was separated from the cells by centrifuging at 15,000×gravity for 10 mins. at 5° C. It was desalted using Sephadex G-50 (Pharmacia, Piscataway, New Jersey). The desalted extract was assayed for EPSP synthase activity as follows:

To an assay mix (40 $\mu$l) containing shikimate-3-phosphate (2 mM), <C-phosphoenolpyruvate (1 mM, 1.2 mCi/mmol), ammonium molybdate (0.1 mM), potassium fluoride (5 mM) in 50 mM HEPES-KOH, pH 7, was added 10 $\mu$l of the extract and incubated at 25° C. for 2 mins. The reaction was quenched by addition of 50 $\mu$l of 90% ethanol/0.1 M acetic acid, pH 4.5. 70 $\mu$l of the reaction mixture was loaded on a SynchroPak AX100 HPLC column (0.4×25 cm) and the column eluted with 0.5 M potassium phosphate, pH 5.5 at 1 ml/min. The radioactivity of the eluent was monitored using a Radiomatic Flo-One Beta Instrument. (Radiomatics, Florida). The EPSP synthase activity was determined by measurement of the conversion of $^{14}$C-PEP to $^{14}$C-EPSP synthase, both of which are resolved under the above conditions of chromatography. The protein content of the extract was determined by the method of Bradford (Biorad Labs, California). The specific activity of the extract is expressed as nanomoles of EPSP synthase formed/min/mg protein.

Assay results show that cells containing pMON9719 had an EPSP synthase activity of about 1600 nanomoles of EPSP synthase formed/minute/mg protein. However, this enzyme was quite sensitive to glyphosate as indicated by an Iso of 12$\mu$M glyphosate. Although cells containing pMON9729 (gly(101)-ala) had a EPSP synthase activity of 390 nanomoles/minute/mg protein, this enzyme was highly glyphosate-tolerant as indicated by an $I_{50}$ value of 32 mM glyphosate.

A plant transformation vector capable of producing the glyphosate resistant form of tomato EPSP synthase in transgenic plants is constructed as follows:

A BglII site is engineered upstream of the ATG translation initiation codon of tomato pre-EPSP synthase by performing site directed mutagenesis on pMON9596. The mutagenesis is performed by the method of Kunkel (1985) using the oligodeoxynucleotide:

5'-GCCATTTCTTGTGAAAAAGATCTTT-
CAGTTTTTC-3'

The alanine for glycine substitution is engineered into the coding sequence for M9568 by site directed mutagenesis exactly as described above. The 700 bp EcoRI/BamHI fragment of the resulting phage is then transferred into EcoRI/BamHI digested pMON9718 replacing the corresponding wild-type fragment.

The 70 bp BglII/EcoRI fragment of the altered pMON9596 is then combined with the 1.6 kb EcoRI/HindIII fragment of the M9718 derivative into BglII/HindIII digested pMON550. pMON550 is a derivative of pUC19 (Yanisch-Perron et al., 1985) produced by inserting the synthetic DNA fragment:

5'-AGCTTTCTAGAAGATCTCCATGGAGGCCTGGTAC-3'
3'-AAGATCTTCTAGAGGTACCTCCGGAC-5' into pUC19 digested with HindIII and Kpn I. This reconstitutes a complete tomato EPSP synthase precursor gene which includes the alanine for glycine substitution.

For insertion into a plant transformation vector a convenient site is engineered at the 3'-end of the coding sequence by digestion with HindIII, making the ends blunt and inserting a ClaI linker (New England Biolabs). The 1.7 kb BglII/ClaI fragment of this plasmid is then inserted into BglII/Cla digested plant transformation vector such as pMON316. The resulting plasmid has the tomato EPSP synthase precursor coding sequence with the alanine for glycine substitution at position 101 of the mature EPSP synthase sequence under control of the CaMV35S promoter. Transformation of plants, such as tomato, with this vector leads to the production of a high level of the glyphosate-tolerant enzyme, resulting in glyphosate tolerant plants.

III. EPSP SYNTHASE OF ARABIDOPSIS

An *Arabidopsis thaliana* genomic bank was prepared by cloning size fractionated (15-20 kb) MboI partially digested DNA into BamHI and EcoRI digested lambda EMBL3 (Strategene Cloning Systems, San Diego, CA). Approximately 10,000 plaques of phage from this library were screened with $^{32}P$ labeled petunia EPSP synthase probe (pMON9566 described hereinbefore). A strongly hybridizing plaque, designated E1, was purified. Southern blots of the EPSP synthase probe to the phage DNA identified two fragments which hybridized very strongly. The first fragment was a 1.0 kb HindIII fragment and the other was a 700 bp BamHI fragment. These fragments were subcloned into plasmid pUC119 and designated pMON574 and pMON578.

Figure 8:
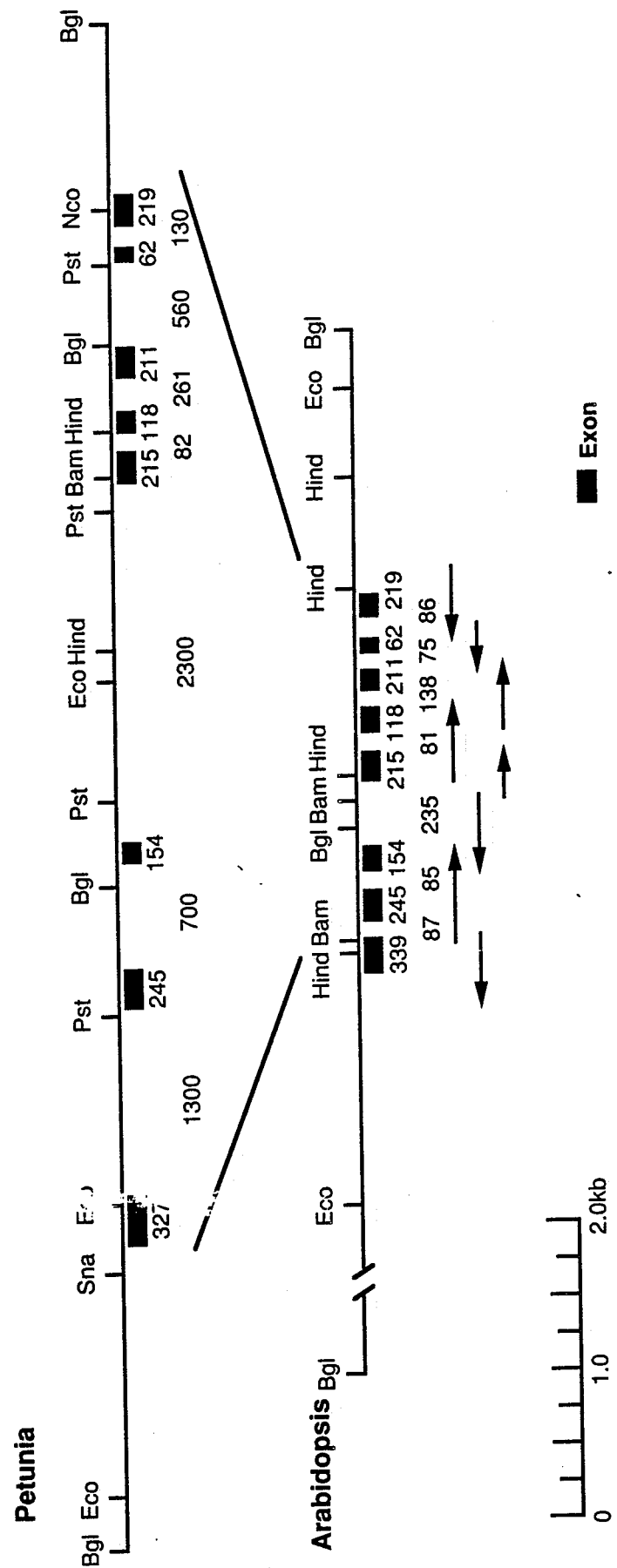
FIG. 8 shows a diagrammatic comparison of the genomic clones of EPSP synthase of petunia and arabidopsis.

The DNA sequences for the two inserts were then determined by the method of Sanger (1977). The sequence data indicated that the phage did contain the EPSP synthase gene of Arabidopsis by its strong homology to the petunia EPSP synthase sequence. The 700 bp BamHI fragment was used as a hybridization probe against the phage and Arabidopsis genomic DNA to identify restriction fragments suitable for the cloning of the entire EPSP synthase gene. Two hybridizing BglII fragments of 6.0 kb and 3.2 kb were identified in the E1 phage clone. These fragments were separately subcloned into pMON550 to provide DNA for further experiments and designated pMON582 and pMON583, respectively. Two additional subclones were made from clones pMON582 and pMON583. Plasmid pMON584 is the 1.8 kb EcoRI to BamHI fragment containing the 5'-end of the Arabidopsis EPSP synthase gene in pUC118 which is prepared from pUC18 in a manner analogous to the preparation of pUC119 from pUC19. Plasmid pMON589 is the 2.8 kb BamHI to BglII fragment containing the 3'-end of the Arabodopsis EPSP synthase gene in pUC119. Sequence determination from the BamHI site of pMON584, and from the BamHI site of pMON589 completed the sequence of the coding regions of the gene, see FIG. 8.

The coding sequence was altered so that the expressed Arabidopsis EPSP synthase would include the alanine for glycine substitution at position 101 of the mature enzyme. Plasmid pMON578 was mutagenized with the oligonucleotide:

5'-CTTTACCTCGGTAATGCAGCTACAG-
CAATGCG-3' by the method of Kunkel (1985). A portion of the resulting plasmid, pMON594, was sequenced to verify the mutation.

A ClaI site is required just upstream of the translational initiation site for insertion of the Arabidopsis EPSP synthase gene into plant transformation/expression vectors. A 370 bp SnaBI/BamHI fragment of pMON584 including the translational initiation site and 65 bp of 5'-untranslated region was cloned into EcoRV/BamHI digested Bluescript KS (Stratagene Cloning Systems, San Diego, CA) forming pMON9734. This fragment can now be removed from pMON9734 with ClaI and BamHI.

The entire Arabidopsis gene was reconstructed for plant transformation experiments as follows: the 3.0 kb BamHI to BglII fragment containing the 3' half of the gene was excised from pMON583 and inserted into the unique BamHI site of pMON9734. This plasmid pMON588, has a unique BamHI site in the middle of the gene. The 800 bp BamHI fragment from pMON594 was then inserted into the unique BamHI site of pMON588. This resulting plasmid, pMON598, contains the entire EPSP synthase gene with the alanine for glycine substitution at position 101 of the mature protein. The entire gene was excised from pMON598 as a 3.5 kb ClaI to EcoRI fragment and cloned into ClaI/EcoRI cut pMON857. This new plasmid, pMON600, contains the entire Arabidopsis gene under the transcriptional control of the CaMV35S promoter and includes the 3' end of the nopaline synthase gene. The plasmid was then introduced into Agrobacterium A208ASE containing the disarmed Ti plasmid pTiT37SE.

Plasmid pMON857 was prepared as follows. The DNA coding sequence for a type IV gentamicin-3-Nacetyltransferase (AAC(3)-IV) enzyme was excised from plasmid pLG62 (Gritz and Davies, 1984). The DNA sequence of this AAC(3)-IV enzyme has been reported in the literature (Brau et al., 1984). Plasmid pMON825 which comprises the DNA containing the open reading frame (ORF) of the AAC(3)-IV enzyme was prepared in the following manner.

A 143 base pair (bp) TaqI fragment spanning the amino terminal portion of the ORF of the AAC(3)-IV gene was excised from pLG62 and cloned into the AccI site of plasmid pUC8 (Vieira et al., 1982) creating pMON823. Next, a 1316 bp SacI-PstI fragment from pLG62 containing the remainder of the ORF was cloned into pMON823 previously cut with SacI and PstI endonucleases. This plasmid was designated pMON824. Plasmid pMON824 contains the reconstructed coding sequence of the type IV gentamicin-3-N-acetyltransferase with an EcoRI site immediately upstream of the start of the ORF. A 1300 bp EcoRI fragment containing the entire ORF was then excised from pMON824 and cloned into the EcoR site of pMON530. This plasmid was designated pMON825. Plasmid pMON825 contains the entire AAC(3)-IV ORF immediately upstream of the NOS 3' transcriptional terminator/polyadenylation signal.

Figure 9:
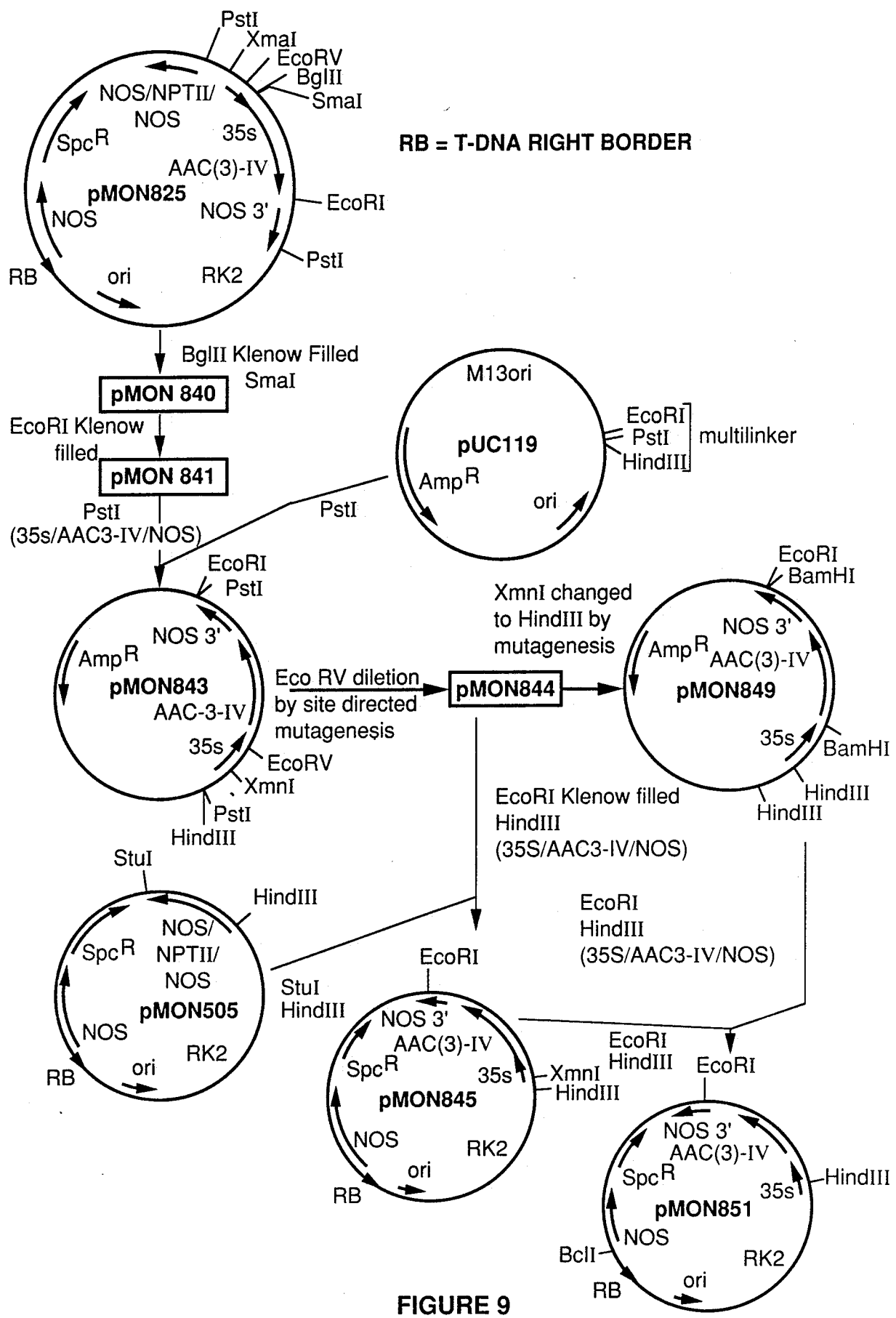
FIG. 9 shows the steps employed in the preparation of plasmid pMON851.

Referring to FIG. 9, plasmid pMON825 was cut with endonucleases SmaI and BglII. The overhangs resulting from the BglII cut were filled by treatment with Klenow polymerase and the four nucleotide triphosphates. The flush ends were ligated by treatment with DNA ligase and the resulting plasmid designated pMON840. Plasmid pMON840 was cut with endonuclease EcoRI. The overhangs were filled by treatment with Klenow polymerase and the four nucleotide triphosphates. The flush ends were ligated by treatment with DNA ligase and the resulting plasmid designated pMON841. The above procedure removed the BglII, SmaI and EcoRI restriction sites from the chimeric CaMV35S/AAC(3)-IV/NOS gene.

Other restriction sites were removed by site directed mutagenesis in the following manner. The 2170 bp PstI fragment of pMON841 was introduced into PstI cut pUC119 producing a construct designated pMON843. The EcoRV site in the CaMV35S promoter sequence was deleted by site directed mutagenesis (Zoller, 1983) using the oligonucleotide:

5'-TTACGTCAGTGGAAGTATCACAT-CAATCCA-3' producing plasmid pMON844. Sequencing confirmed that pMON844 contained the above-described EcoRV deletion.

Figure 10:
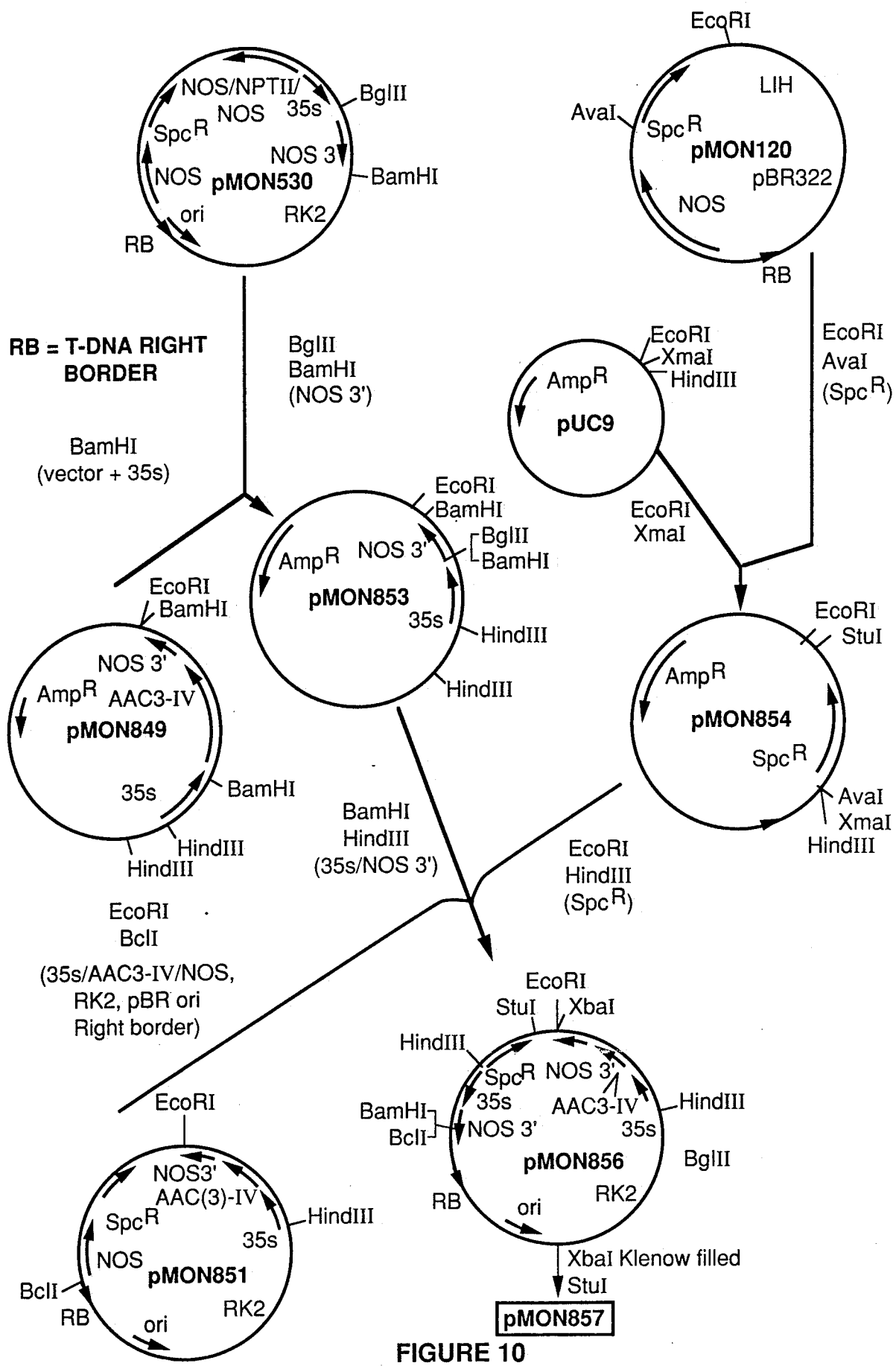
FIG. 10 shows the steps employed in the preparation of plasmid pMON857.

The NOS/NPTII/NOS gene in pMON505 was removed by cleavage of pMON505 with StuI and HindIII. It was replaced with the 2220 bp EcoRI (Klenow filled) HindIII fragment from pMON844 containing the CaMV35S/AAC(3)-IV/NOS gene. This plasmid was designated pMON845. It was subsequently determined by sequence analysis that the CaMV35S/AAC(3)-IV/NOS chimeric gene which is in pMON845 contained extraneous sequence upstream from the start of the CaMV35S promoter sequence carried from the NOS promoter of pMON825. The XmaI site at the start of the CaMV35S promoter of pMON844 was changed to a HindIII by site directed mutagenesis using the oligonucleotide:

5'-TGTAGGATCGGGAAGCTTCCCCGGAT-CATG-3' producing plasmid pMON849. The EcoRI/HindIII fragment of pMON845 (containing the CaMV35-S/AAC(3)-IV/NOS gene) was replaced with the smaller 1900 bp EcoRI/HindIII fragment of pMON849 carrying the same chimeric gene. This plasmid was designated pMON851. Fragments were used from three plasmids to construct a multipurpose cloning vector employing the CaMV35S/AAC(3)-IV/NOS gene as a selectable marker and containing a CaMV35S/NOS3' cassette. Referring to FIG. 10, the CaMV35S/NOS3' cassette was prepared from pMON849 and pMON530. Specifically, pMON849 was cut with BamHI removing the AAC(3)-IV/NOS sequence while leaving the CaMV35S sequence. The 294 bp BglII/BamHI fragment from pMON530 containing the multilinker and NOS3' was ligated into the BamHI cut pMON849 producing pMON853.

The Tn7 Spc/Str resistance gene was obtained from pMON120. The 1600 bp EcoRI/AraI fragment of pMON120 containing the Spc/Str gene was cloned into EcoRI and XmaI cut pUC9 producing plasmid pMON854.

Plasmid pMON856 was prepared by ligation of the following three fragments:

Fragment #1: The 7770 bp EcoRI to BclI fragment from pMON851 containing the CaMV35S/AAC(3)-IV/NOS selectable marker gene, RK2 replicon, pBR322 origin of replication, and the right border sequence from plasmid pTiT37 of *Agrobacterium tumefaciens*.

Fragment #2: The 630 bp HindIII to BamHI fragment from pMON853 containing the CaMV35S/NOS3' cassette and the multilinker.

Fragment #3: The 1630 bp HindIII to BamHI fragment from pMON854 containing the Spc/Str resistance gene.

Extraneous sequence and restriction sites between the selectable marker gene and the Spc/Str gene were removed from pMON856 in the following manner. Plasmid pMON856 was cut with StuI and XbaI. The XbaI site was filled by treatment with Klenow polymerase and the four nucleotide triphosphates. Subsequent ligation produced plasmid pMON857 which is a useful plant transformation vector containing the CaMV35-S/AAC(3)-IV/NOS selectable marker gene.

The *Agrobacterium* harboring the pMON600 plasmid was used to transform explants of *Brassica napus*. Three gentamicin resistant calli were obtained. All three of these calli were found to be capable of growth on 0.5 mM glyphosate, a concentration which kills wild type callus. Proteins were extracted from samples of the calli and were assayed for EPSP synthase activity. All three of the calli contained EPSP synthase activity that was resistant to 0.5 mM glyphosate.

These results demonstrate that the calli transformed with pMON600 contain a glyphosate resistant form of EPSP synthase. The EPSP synthase in the extracts was further characterized by titrating the resistance to glyphosate. The $I_{50}$ of the enzyme was found to be 7.5 mM, this is several orders of magnitude higher than has been found for any wild type plant EPSP synthase. Given the differences in the conditions of the assays (plant extracts which still contain the endogenous (wild-type) EPSP synthase versus extracts from overproducing *E. coli*) this $I_{50}$ does not differ significantly from the values found for the petunia and tomato enzymes carrying the same alanine for glycine substitution (16 and 32 mM respectively).

Plants transformed with plasmid pMON600 are produced by transforming stem explants and culturing under selective conditions which favor shoot formation over callus formation. The resulting plants will contain the glyphosate-tolerant form of EPSP synthase and will exhibit elevated tolerance to glyphosate herbicide.

IV. EPSP SYNTHASE OF Glycine max

The cDNA for EPSP synthase of Glycine max was isolated from a library constructed from RNA isolated from Glycine max root tips. The library was constructed using the commercially available Amersham cDNA synthesis kit (Amersham Corp., Arlington Hts., IL), and lambda gt10 from Vector Cloning Systems (San Diego, CA). The library was screened with an insert from pMON578 which contains part of the EPSP synthase gene and hybridizing plaques were isolated and their inserts subcloned into Bluescript plasmids (Vector Cloning Systems, San Diego, CA), and single stranded phage. The sequence of a portion of one of the cDNA clones (pMON9752, containing a 1600 bp cDNA) was determined. Referring to FIG. 2, the protein deduced from the nucleotide sequence has strong homology to the petunia sequence in the region corresponding to the mature protein. Notably, amino acids 94–107 of the petunia enzyme are identical to amino acids 97–110 of the mature Glycine max enzyme (a three amino acid insertion in the Glycine max relative to the petunia near the amino terminus is responsible for the difference in numbering, see FIG. 2).

The Glycine max enzyme was altered to change the glycine at position 104 (which corresponds to Gly 101 in petunia) to an alanine by site directed mutagenesis using the oligonucleotide:

5'-AAAGGACGCATTGCACTGGCAGCATTT-CCAA-3' according to the method of Kunkel (1985).

Initial cDNA clones isolated did not contain the complete sequence of the amino terminal chloroplast transit peptide of Glycine max EPSP synthase. The remaining sequence is isolated by screening the cDNA library until a clone containing this region is obtained or by isolating a clone from a library of Glycine max genomic DNA by hybridization with a Glycine max cDNA clone. For expression in plants a BglII or other convenient site is engineered just upstream of the normal translational initiation codon as was done in the petunia and tomato sequences. This region is then combined with the cDNA that had been mutagenized to contain the alanine for glycine substitution at a common HindIII site. The altered gene is then inserted into a plant transformation vector such as pMON530 which places the coding sequence under the control of the CaMV35S promoter. The resulting vector is used to produce transgenic plants which exhibit enhanced tolerance to glyphosate herbicide.

Preparation of a Glyphosate Tolerant Maize EPSP Synthase Gene, and Glyphosate Tolerant Maize Cells Construction of a glyphosate tolerant maize gene Maize seeds were imbibed for 12 hr in water, the embryos including the scutella were dissected from the seeds and RNA was purified from this material by the method of Rochester et al. (1986). PolyA-mRNA was isolated from the RNA by chromatography on oligo dT cellulose, and was used to construct a cDNA library as described previously. The library was screened with a $^{32}$-P labelled RNA probe synthesized in vitro from pMON9717 which had been linearized with HindIII. The probe was synthesized with T7 RNA polymerase (Promega, Madison, WI) according to the manufacturers instructions. Hybridizing plaques were isolated, replated, and nitrocellulose lifts from the plates were screened with the same probe. Plaques representing single clones which hybridized strongly to the tomato probe were isolated, propagated and used to prepare DNA. Clone lambda-zld was found to contain a 1.8 kb EcoRI insert. The insert of this phage was subcloned into the EcoRI site of Bluescript KS+(Strategene, San Diego, CA) to form pMON9935. The complete sequence of this cDNA clone was determined and is shown in FIG. 2. To facilitate future constructions an Xba I site was engineered immediately upstream of the first ATG initiation codon of this clone by oligonucleotide mediated mutagenesis by the method of Kunkel using the oligonucleotide:

5'-TACCAACCATCGGCGTCTAGAGG-CAATGGCGGC-3' producing plasmid pMON9950. pMON9950 was digested with Xba I and religated to eliminate the 126 bp Xba I fragment at the 5' end of the cDNA forming pMON9951. To produce a coding sequence for a glyphosate tolerant form of maize EPSP synthase pMON9951 was mutated by the method of Kunkel using the oligonucleotide:

5'-CTTCTTGGGGAATGCTGCTACT-GCAATGCGGC-3' resulting in pMON9960. This mutagensis will change a GGA codon to a GCT codon, changing the second glycine residue in the conserved sequence -L-G-N-A-G-T-A- to an alanine in the resulting protein. The glycine residue is amino acid 163 of the predicted maize preEPSP synthase. This would correspond to amino acid 95–105 of the mature protein depending on the precise transit peptidase cleavage site which has not been determined.

To demonstrate that this alteration produced a glyphosate tolerant form of maize EPSP synthase, protein was produced from pMON9951 and pMON9960 by in vitro transcription with T7 RNA polymerase, followed by in vitro translation as follows: Plasmid DNA (pMON9951 and pMON9960) containing the full-length EPSP synthase cDNA was linearized with EcoRI. The linearized plasmid DNA was transcribed in vitro with T7 polymerase essentially as described by Krieg et al., 1984. The standard reaction buffer contained 40 mM Tris-HCl (pH 7.9), 6 mM MgCl$_2$, 10 mM dithiothreitol, 2 mM spermidine, 80 U RNAsin ribuonuclease inhibitor, 0.5 mM each of ATP, GTP, CTP and UTP, in a final reaction volume of 100 μl. The final RNA pellet was resuspended in 20 μl of sterile water and stored at −80° C. A standard translation reaction contained 100 μl of nuclease-treated rabbit reticulocyte lysate, 5.7 μl of a 19-amino acid mixture (minus methionine at 1 mM each, 5.7 μl of RNA (total RNA transcripts derived from 0.63 μg of plasmid DNA), 16 μl RNAsin (20U/μl) ribonuclease inhibitor, and 58.3 μl of [$^{35}$S] methionine (14–15 mCi/ml). The in vitro translation products were stored frozen at −80° C.

Figure 12:
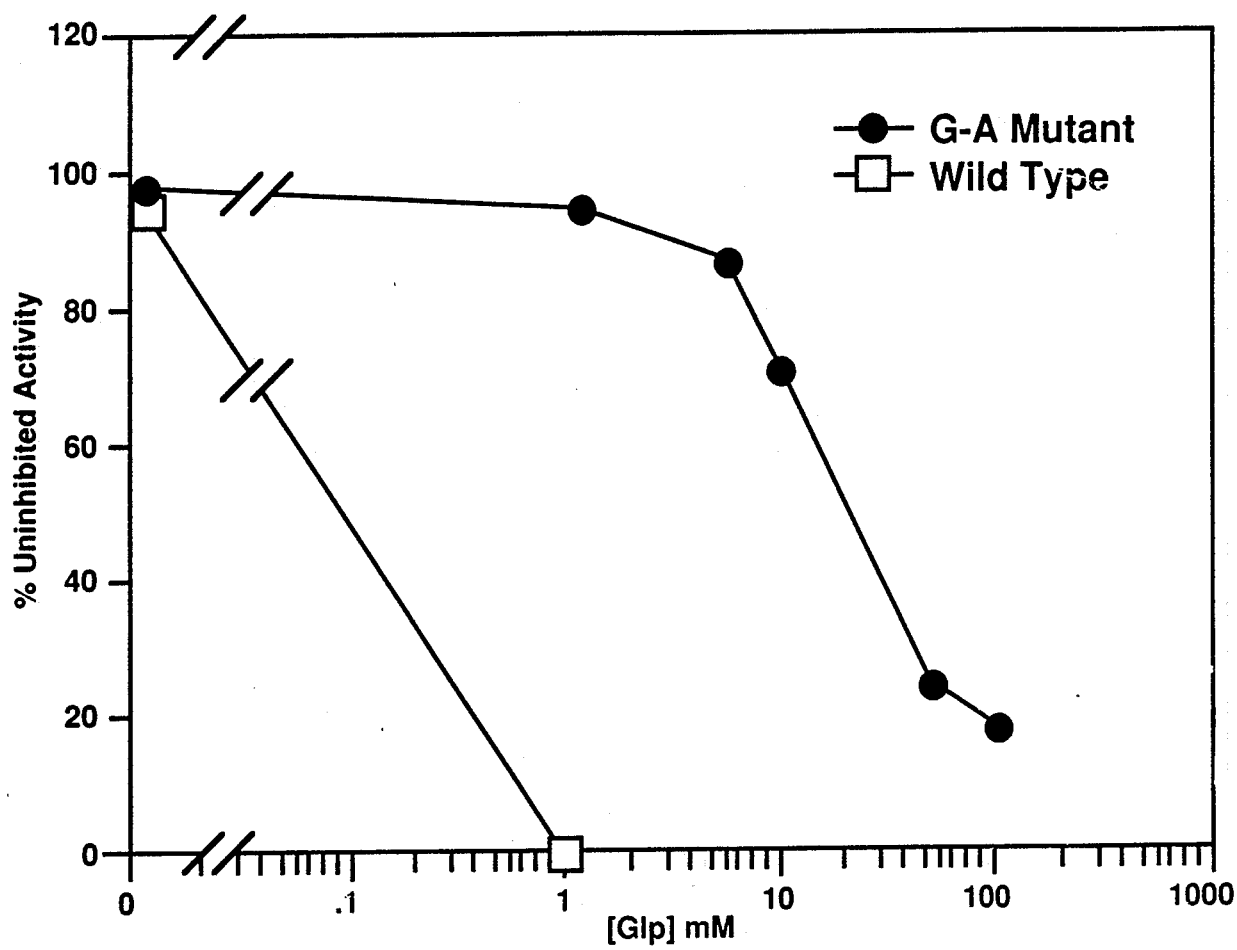
FIG. 12 illustrates the glyphosate tolerance of the mutant maize EPSP synthase of the present invention versus the wild-type maize EPSP synthase.

The products of the in vitro translation were then assayed for EPSP synthase activity as described herein. Referring to FIG. 12, the product of pMON9951 showed easily detectable EPSP synthase activity in the absence of glyphosate. When the assay was repeated in the presence of 1.0 mM glyphosate no activity was detected. In contrast the mutant pre-enzyme product of pMON9960 showed a high level of tolerance to glyphosate, being only slightly inhibited at 1 mM glyphosate, was 25% inhibited at 10 mM glyphosate and still showing detectable activity at 100 mM glyphosate.

For expression in maize cells the coding sequence of the glyphosate tolerant mutant form of maize pre-EPSP synthase is excised from pMON9960 and inserted between a promoter known to function in maize cells such as the CaMV35S promoter, and the poly A addition site of the nopaline synthase gene. In addition an intron such as the first intron of the maize ADH1 gene may be included in the 5'-untranslated region of the expression unit which may enhance expression of the chimeric gene (Callis, et al. 1987).

This expression unit is then inserted into a vector which includes the neomycin phosphotransferase gene under control of the CaMV35S promoter, or a similar vector with a marker gene that can allow for selection of transformed maize cells. This vector, or a similar vector using any other glyphosate resistant coding sequence constructed as described in the claims and examples of this application is then introduced into maize cells as described in the following example.

Preparation of Maize Protoplasts

Protoplasts are prepared from a Black Mexican Sweet (BMS) maize suspension line, BMSI (ATCC 54022) as described by Fromm et al. (1985 and 1986). BMSI suspension cells are grown in BMS medium which contains MS salts, 20 g/l sucrose, 2 mg/l (2,4-dichlorophenoxy) acetic acid, 200 mg/l inositol, 130 mg/l asparagine, 1.3 mg/l niacin, 0.25 mg/l thiamine, 0.25 mg/l pyridoxine, 0.25 mg/l calcium pantothenate, pH 5.8. 40 ml cultures in 125 erlenmeyer flasks are shaken at 150 rpm at 26° C. The culture is diluted with an equal volume of fresh medium every 3 days. Protoplasts are isolated from actively growing cells 1 to 2 days after adding fresh medium. For protoplast isolation cells are pelleted at 200×g in a swinging bucket table top centrifuge. The supernatant is saved as conditioned medium for culturing the protoplasts. Six ml of packed cells are resuspended in 40ml of 0.2 M mannitol/50 mM CaCl2/10 mM sodium acetate which contains 1% cellulase, 0.5% hemicellulase and 0.02% pectinase. After incubation for 2 hours at 26° C., protoplasts are separated by filtration through a 60 um nylon mesh screen, centrifuged at 200×g, and washed once in the same solution without enzymes.

Transformation of Maize Protoplasts Using an Electroporation Technique

Protoplasts are prepared for electroporation by washing in a solution containing 2 mM potassium phosphate pH 7.1, 4 mM calcium chloride, 140 mM sodium chloride and 0.2 M mannitol. After washing, the protoplasts are resuspended in the same solution at a concentration of 4 X 10E6 protoplasts per ml. One-half ml of the protoplast containing solution is mixed with 0.5 ml of the same solution containing 50 micrograms of supercoiled plasmid vector DNA and placed in a 1 ml electroporation cuvette. Electroporation is carried out as described by Fromm et al. (1986). As described, an electrical pulse is delivered from a 122 or 245 microFarad capacitor charged to 200 V. After 10 minutes at 4° C. and 10 min at room temperature protoplasts are diluted with 8 ml of medium containing MS salts 0.3 M mannitol, 2% sucrose, 2 mg/l 2,4-D, 20% conditioned BMS medium (see above) and 0.1% low melting agarose. After 2 weeks in the dark at 26° C., medium without mannitol and containing kanamycin is added to give a final concentration of 100 mg/l kanamycin. After an additional 2 weeks, microcalli are removed from the liquid and placed on a membrane filter disk above agarose-solidified medium containing 100 mg/l kanamycin. Kanamycin resistant calli composed of transformed maize cells appear after 1-2 weeks.

Glyphosate tolerant maize cells

As described by Fromm et al. (1986), transformed maize cells can be selected by growth in kanamycin-containing medium following electroporation with DNA vectors containing chimeric kanamycin resistance genes composed of the CaMV35S promoter, the NPTII coding region and the NOS 3' end. These cells would also be producing the glyphosate tolerant form of EPSP synthase, and would tolerate elevated levels of glyphosate.

Alternative methods for the introduction of the plasmids into maize, or other monocot cells would include, but are not limited to, the high-velocity microprojectile method of Klein et al. (1987) or the injection method of de la Pena et al. (1987).

The embodiments described above are provided to better elucidate the practice of the present invention. It should be understood that these embodiments are provided for illustrative purposes only, and are not intended to limit the scope of the invention.

REFERENCES

Adams, S.P. and Galluppi, G. R. (1986) *Medicinal Research Reviews* 6:135-170.

Adams, S.P., et al., (1983) *J. Amer. Chem. Soc.* 05:661.

Ausubel, F., et al., (1980) *Plant Mol. Bio. Newsletter* 1:26-32.

Brau, et al., *Mol. Gen. Genet.* 193:179-187 (1984).

Broglie, R. et al., (1983) *Bio/Technology* 1:55-61.

Callis, J., Fromm, M. and Walbot, V. (1987) *Genes and Develop.* 1:1183-1200.

Charles, G. Keyte, J. W., Brammer, W. J., Smith, M. and Hawkins, A. R. (1986) *Nucleic Acids Res.* 14:2201-2213.

Covey, S., Lomonosoff, G. and Hill, R., (1981) *Nucleic Acids Res.* 9:6735.

de la Pena, A., Lorz, H. and Schell, J. (1987) *Nature* 325:274-276.

DePicker A., et al., (1982) *J. Mol. Appl. Gen.* 1:561.

Ditta, G., et al., (1980) *Pro. Natl. Acad. Sci. USA* 77:7347.

Duncan, K., Lewendon, A. and Coggins, J. R. (1984) *FEBS Lett.* 170:59-63.

Fraley, R., Rogers, S., Eichholtz, D., Flick, J., Fink, C., Hoffman, N. and Sanders, P., (1985) *Bio/Technology* 3:629.

Fromm, M., Taylor, L. P. and Walbot, V. (1985) *Proc. Nat Acad. Sci. USA* 82:5824-5828.

Fromm, M., Taylor, L. P. and Walbot, V. (1986) *Nature* 319:791-793.

Gardner, R., Howarth, A., Hahn, P., Brown-Luedi, M., Shepherd, R. and Messing, J., (1981) *Nucleic Acids Res.* 9:2871.

Gritz and Davies, *Gene* 25:179-188 (1984).

Guilley, H., Dudley, R., Jonard, G., Balax, E. and Richards, K. (1982) *Cell* 30:763.

Goldberg, R. B., et al., (1981) *Devel. Bio.* 83:201-217.

Gubler, U., and Hoffman, B. H. (1983) *Gene* 25:263-269.

Horsch, R. and Klee, H., (1986) *Proc. Natl. Acad. Sci. USA* vol. 83, 4428-4432.

Horsch, R. B., and Jones, G. E. (1980) *In Vitro* 16:103–108.

Horii, T., et al. (1980) *P.N.A.S. USA* 77:313.

Hunkapiller, M. W., et al. (1983b) *Methods Enzymol.* 91:486–493.

Huynh, T.V. Young, R.A. and Davis, R.W. (1985) DNA *Cloning Techniques: A Practical Approach*, D. Glover ed., IRL Press, Oxford.

Klein, T.M., Wolf, E.D., Wu, R. and Sanford, J.C. (1987) *Nature* 327:70–73.

Krieg, P.A. and Melton, D.A. (1984) *Nucleic Acids Res.* 12:7057–7070.

Kunkel (1985) *P.N.A.S. USA* 82:488–492.

Lemke, G. and Axel, R. (1985) *Cell* 40:501–508.

Maniatis, T., et al. (1982) *Molecular Cloning: A Laboratory Manual*, Cold Spring Harbor Labs., NY.

Marmur, J. (1961) *J. Mol. Biol.* 3:208–210.

Maxam, A.M. and Gilbert, W., (1977) *P.N.A.S. USA* 74:560–564.

Messing, J. et al. (1981) *Nucleic Res.* 9:309–321.

Mousdale, D.M. and Doggins, J.R. (1984) *Planta* 160:78–83.

Okayama, H. and Berg, P. (1982) *Mol. Cell. Biol.* 2:161.

Rao, R.N. and Rogers, S.G. (1979) Gene pp. 7:79–82.

Rochester, D.E., Winter, J.A. and Shah, D.M. (1986) *EMBO J.* 5:452–458.

Rogers, S., Horsch, R. and Fraley, R., (1986) *Methods in Enzymology* Vol. 118 (H. Weissbach and A. Weissbach, eds.) p.627, Academic Press, New York.

Rogers, S.G., et al. (1983) *Appl. Envir. Microbio.* 46:37–43.

Sancar, A., et al. (1980) *P.N.A.S. USA* 77:2611.

Sanger, et al. (1977) *Proc. Natl. Acad. Sci. USA* 74:5463.

Scherer, et al. (1981) *Developmental Bio.* 86:438–447.

Schimke, R.T. ed. (1982) *Gene Amplification*, Cold Spring Harbor Labs.

Schmidhauser, T. and Helinski, D. (1985) *J. Bacteriology* 164:446.

Soberson, et al. (1980), *Gene* 9:287–305.

Southern, E.M. (1975) *J. Mol. Biol.* 98:503–517.

Stalker, D. M., Hiatt, W. R. and Comai, L. (1985) *J. Biol Chem.* 260:4724–4728.

Steinrucken, H. and Amrhein, N. (1980) *Biochem. & Biophys. Res. Comm.* 94:1207–1212.

Vieira, J. et al., (1982) *Gene* 19:259–268.

Yanisch-Perron, C., Vieira, J. and Messing, J. (1985) *Gene* 33:103–119.

Zoller, M.M. et al. (1983) *Methods Enzymol.* 100:468.

We claim:

1. A method for producing a gene encoding a glyphosate-tolerant 5-enolpyruvyl-3-phosphoshikimate (EPSP) synthase enzyme which comprises altering a gene encoding EPSP synthase to cause the substitution of an alanine residue for the second glycine residue in the amino acid sequence:

-L-G-N-A-G-T-A- located between positions 80 and 120 in a mature EPSP synthase sequence.

2. A method of claim 1 in which the glyphosate-tolerant EPSP synthase gene is produced from a plant EPSP synthase gene.

3. A method of claim 1 in which the glyphosate-tolerant EPSP synthase gene is produced from a bacterial EPSP synthase gene.

4. A method of claim 1 in which the glyphosate-tolerant EPSP synthase gene is produced from a fungal gene encoding EPSP synthase.

5. A glyphosate-tolerant 5-enolpyruvyl-3-phosphoshikimate (EPSP) synthase enzyme which contains the amino acid sequence:

-L-G-N-A-A-T-A- between positions 80 and 120 in the mature EPSP synthase sequence.

6. The glyphosate-tolerant EPSP synthase enzyme of claim 5 as shown in FIGS. 1(a) and 1(b).

7. A glyphosate-tolerant EPSP synthase gene produced by the method of claim 1 wherein the wild-type EPSP synthase coding sequence is selected from the group of EPSP synthases consisting of *Aspergillus nidulans*, petunia, tomato, maize, *Arabidopsis thaliana, Glycine max, E. coli* K-12 and *Salmonella typhimurium* as shown in FIG. 2.

8. A glyphosate-tolerant EPSP synthase gene of claim 7 wherein the wild-type EPSP synthase coding sequence is selected from *Aspergillus nidulans*.

9. A glyphosate-tolerant EPSP synthase gene of claim 7 wherein the wild-type EPSP synthase coding sequence is selected from petunia.

10. A glyphosate-tolerant EPSP synthase gene of claim 7 wherein the wild-type EPSP synthase coding sequence is selected from tomato.

11. A glyphosate-tolerant EPSP synthase gene of claim 7 wherein the wild-type EPSP synthase coding sequence is selected from maize.

12. A glyphosate-tolerant EPSP synthase gene of claim 7 wherein the wild-type EPSP synthase coding sequence is selected from *Arabidopsis thaliana*.

13. A glyphosate-tolerant EPSP synthase gene of claim 7 wherein the wild-type EPSP synthase coding sequence is selected from *Glycine max*.

14. A glyphosate-tolerant EPSP synthase gene of claim 7 wherein the wild-type EPSP synthase coding sequence is selected from *E. coli* K-12.

15. A glyphosate-tolerant EPSP synthase gene of claim 7 wherein the wild-type EPSP synthase coding sequence is selected from *Salmonella typhimurium*.

* * * * *